US012599772B2

(12) United States Patent
Zhang et al.

(10) Patent No.: US 12,599,772 B2
(45) Date of Patent: *Apr. 14, 2026

(54) SELECTION OF SENSING ELECTRODES IN A SPINAL CORD STIMULATOR SYSTEM USING SENSED STIMULATION ARTIFACTS

(71) Applicant: Boston Scientific Neuromodulation Corporation, Valencia, CA (US)

(72) Inventors: Tianhe Zhang, Studio City, CA (US); Rosana Esteller, Santa Clarita, CA (US); Thomas W. Stouffer, Chatsworth, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 36 days.

This patent is subject to a terminal disclaimer.

(21) Appl. No.: 18/736,300

(22) Filed: Jun. 6, 2024

(65) Prior Publication Data

US 2024/0316352 A1 Sep. 26, 2024

Related U.S. Application Data

(63) Continuation of application No. 17/133,040, filed on Dec. 23, 2020, now Pat. No. 12,023,505.

(Continued)

(51) Int. Cl.
*A61N 1/00* (2006.01)
*A61B 5/311* (2021.01)
(Continued)

(52) U.S. Cl.
CPC .......... *A61N 1/37235* (2013.01); *A61B 5/311* (2021.01); *A61B 5/388* (2021.01); *A61N 1/0551* (2013.01); *A61N 1/36135* (2013.01)

(58) Field of Classification Search
CPC .............. A61N 1/37235; A61N 1/0551; A61N 1/36135; A61N 1/36139; A61N 1/36185;
(Continued)

(56) References Cited

U.S. PATENT DOCUMENTS

| 6,163,724 A | 12/2000 | Hemming et al. |
| 6,181,969 B1 | 1/2001 | Gord |

(Continued)

FOREIGN PATENT DOCUMENTS

WO 2020/251899 12/2020

OTHER PUBLICATIONS

International Search Report and Written Opinion regarding corresponding PCT Application No. PCT/US2020/066911, mailed Mar. 19, 2021.

*Primary Examiner* — Scott M. Getzow
(74) *Attorney, Agent, or Firm* — Lewis & Reese, PLLC

(57) ABSTRACT

A sensing electrode selection algorithm is disclosed for use with an implantable pulse generator having an electrode array. The algorithm automatically selects optimal sensing electrodes in the array to be used with a pre-determined stimulation therapy appropriate for the patient. The algorithm preferably senses stimulation artifacts using different sensing electrodes, and more specifically different sensing electrode pairs as is appropriate when differential sensing is used. The algorithm further preferably senses these stimulation artifacts with the patient placed in two or more postures. The algorithm processes the stimulation artifact features measured at the different sensing electrodes and at the different postures to automatically determine one or more sensing electrode pairs that best distinguishes the two or more postures given the prescribed stimulation therapy.

18 Claims, 18 Drawing Sheets

Related U.S. Application Data

(60) Provisional application No. 62/970,448, filed on Feb. 5, 2020.

(51) Int. Cl.

| | | |
|---|---|---|
| *A61B 5/388* | (2021.01) | |
| *A61N 1/05* | (2006.01) | |
| *A61N 1/36* | (2006.01) | |
| *A61N 1/372* | (2006.01) | |

(58) Field of Classification Search

CPC ............ A61N 1/37241; A61N 1/36062; A61B 5/311; A61B 5/388; A61B 5/1116; A61B 5/4836; A61B 5/7235; A61B 5/407; A61B 5/686; A61B 5/7217; A61B 5/4833

See application file for complete search history.

(56) References Cited

U.S. PATENT DOCUMENTS

| | | | |
|---|---|---|---|
| 6,516,227 | B1 | 2/2003 | Meadows et al. |
| 8,190,258 | B2 | 5/2012 | Armstrong |
| 8,606,362 | B2 | 12/2013 | He et al. |
| 8,620,436 | B2 | 12/2013 | Parramon et al. |
| 9,259,574 | B2 | 2/2016 | Aghassian et al. |
| 9,814,885 | B2 | 11/2017 | Molnar et al. |
| 10,406,368 | B2 | 9/2019 | Hershey et al. |
| 2006/0195159 | A1 | 8/2006 | Bradley et al. |
| 2007/0066998 | A1 | 3/2007 | Hansen et al. |
| 2012/0092031 | A1 | 4/2012 | Shi et al. |
| 2012/0095519 | A1 | 4/2012 | Parramon et al. |
| 2012/0095529 | A1 | 4/2012 | Parramon et al. |
| 2013/0289665 | A1 | 10/2013 | Marnfeldt et al. |
| 2015/0080982 | A1 | 3/2015 | Funderburk |
| 2015/0157861 | A1 | 6/2015 | Aghassian |
| 2015/0231402 | A1 | 8/2015 | Aghassian |
| 2015/0360038 | A1 | 12/2015 | Zottola et al. |
| 2018/0071520 | A1 | 3/2018 | Weerakoon et al. |
| 2018/0071527 | A1 | 3/2018 | Feldman et al. |
| 2018/0140831 | A1 | 5/2018 | Feldman et al. |
| 2019/0070418 | A1 | 3/2019 | Hincapie Ordonez et al. |
| 2019/0076645 | A1 | 3/2019 | Bower et al. |
| 2019/0076659 | A1 | 3/2019 | Steinke et al. |
| 2019/0083796 | A1 | 3/2019 | Weerakoon et al. |
| 2019/0099602 | A1 | 4/2019 | Esteller et al. |
| 2019/0099606 | A1 | 4/2019 | Shah et al. |
| 2019/0175915 | A1 | 6/2019 | Brill et al. |
| 2019/0209844 | A1 | 7/2019 | Esteller et al. |
| 2019/0275331 | A1 | 9/2019 | Zhu |
| 2019/0290900 | A1 | 9/2019 | Esteller et al. |
| 2019/0299006 | A1 | 10/2019 | Marnfeldt |
| 2019/0366094 | A1 | 12/2019 | Esteller et al. |
| 2019/0388692 | A1 | 12/2019 | Dinsmoor et al. |
| 2020/0147393 | A1 | 5/2020 | Zhang et al. |
| 2020/0155019 | A1 | 5/2020 | Esteller et al. |
| 2020/0305744 | A1 | 10/2020 | Weerakoon et al. |
| 2020/0305745 | A1 | 10/2020 | Wagenbach et al. |
| 2021/0187299 | A1 | 6/2021 | Dinsmoor et al. |
| 2022/0233866 | A1 | 7/2022 | Gururaj et al. |
| 2022/0347479 | A1 | 11/2022 | Esteller et al. |

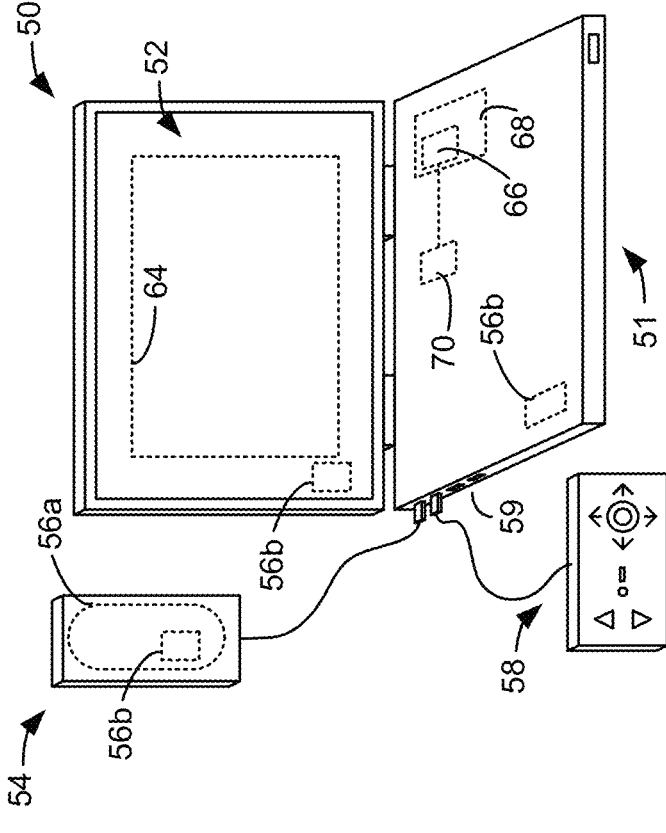
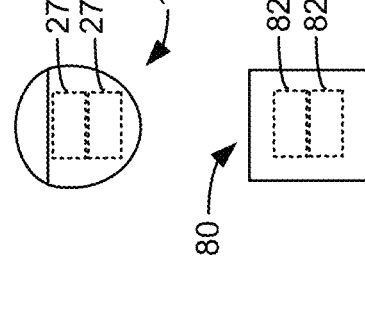
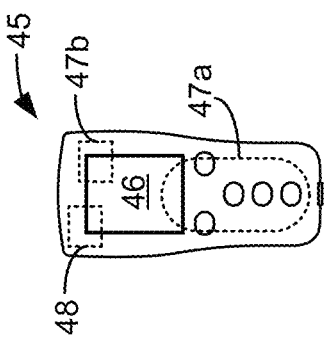
*Figure 4*
*(prior art)*

Sensing electrode selection algorithm 150

150

*Feature Matrix 2 (max Stim Art amplitude): Patient sitting*

| | E1 | E2 | E3 | E4 | E5 | E6 | E7 | E8 | E9 | E10 | E11 | E12 | E13 | E14 | E15 | E16 |
|---|---|---|---|---|---|---|---|---|---|---|---|---|---|---|---|---|
| E16 | 1.5 | x | x | 1.39 | 0.69 | 0.09 | 0.2 | 0 | 0.4 | 0.29 | 0.29 | 0.49 | 0.19 | 0 | 0.04 | x |
| E15 | 1.35 | x | x | 1.35 | 0.65 | 0.05 | 0 | 0.04 | 0.45 | 0.2 | 0.2 | 0.6 | 0.15 | 0.05 | x | 0.04 |
| E14 | 1.3 | x | x | 1.3 | 0.6 | 0 | 0.05 | 0.2 | 0.4 | 0.2 | 0.3 | 0.4 | 0.2 | x | 0.05 | 0 |
| E13 | 1.3 | x | x | 1.2 | 0.4 | 0.1 | 0.15 | 0.1 | 0.3 | 0 | 0.1 | 0.3 | x | 0.2 | 0.15 | 0.19 |
| E12 | 1 | x | x | 1 | 0.2 | 0.4 | 0.45 | 0.49 | 0.2 | 0 | 0.2 | x | 0.3 | 0.4 | 0.6 | 0.49 |
| E11 | 1.1 | x | x | 1.2 | 0.4 | 0.2 | 0.25 | 0.29 | 0.2 | 0 | x | 0.2 | 0.1 | 0.3 | 0.2 | 0.29 |
| E10 | 1.1 | x | x | 1.1 | 0.5 | 0.2 | 0.5 | 0.4 | 0.2 | x | 0 | 0 | 0 | 0.2 | 0.2 | 0.29 |
| E9 | 0.9 | x | x | 0.9 | 0.3 | 0.4 | 0.45 | 0.49 | x | 0.2 | 0.2 | 0.2 | 0.3 | 0.4 | 0.45 | 0.4 |
| E8 | 1.39 | x | x | 1.39 | 0.69 | 0.09 | 0.04 | x | 0.49 | 0.4 | 0.29 | 0.49 | 0.1 | 0.2 | 0.04 | 0 |
| E7 | 1.2 | x | x | 1.35 | 0.65 | 0.05 | x | 0.04 | 0.45 | 0.5 | 0.25 | 0.45 | 0.15 | 0.05 | 0 | 0.2 |
| E6 | 1.3 | x | x | 1.3 | 0.6 | x | 0.05 | 0.09 | 0.4 | 0.2 | 0.2 | 0.4 | 0.1 | 0 | 0.05 | 0.09 |
| E5 | 0.7 | x | x | 0.7 | x | 0.6 | 0.65 | 0.69 | 0.3 | 0.5 | 0.4 | 0.2 | 0.4 | 0.6 | 0.65 | 0.69 |
| E4 | 0.1 | x | x | x | 0.7 | 1.3 | 1.35 | 1.39 | 0.9 | 1.1 | 1.2 | 1 | 1.2 | 1.3 | 1.35 | 1.39 |
| E3 | x | x | x | x | x | x | x | x | x | x | x | x | x | x | x | x |
| E2 | x | x | x | x | x | x | x | x | x | x | x | x | x | x | x | x |
| E1 | x | x | x | 0.1 | 0.7 | 1.3 | 1.2 | 1.39 | 0.9 | 1.1 | 1.1 | 1 | 1.3 | 1.3 | 1.35 | 1.5 |
| | E1 | E2 | E3 | E4 | E5 | E6 | E7 | E8 | E9 | E10 | E11 | E12 | E13 | E14 | E15 | E16 |

S-

S+

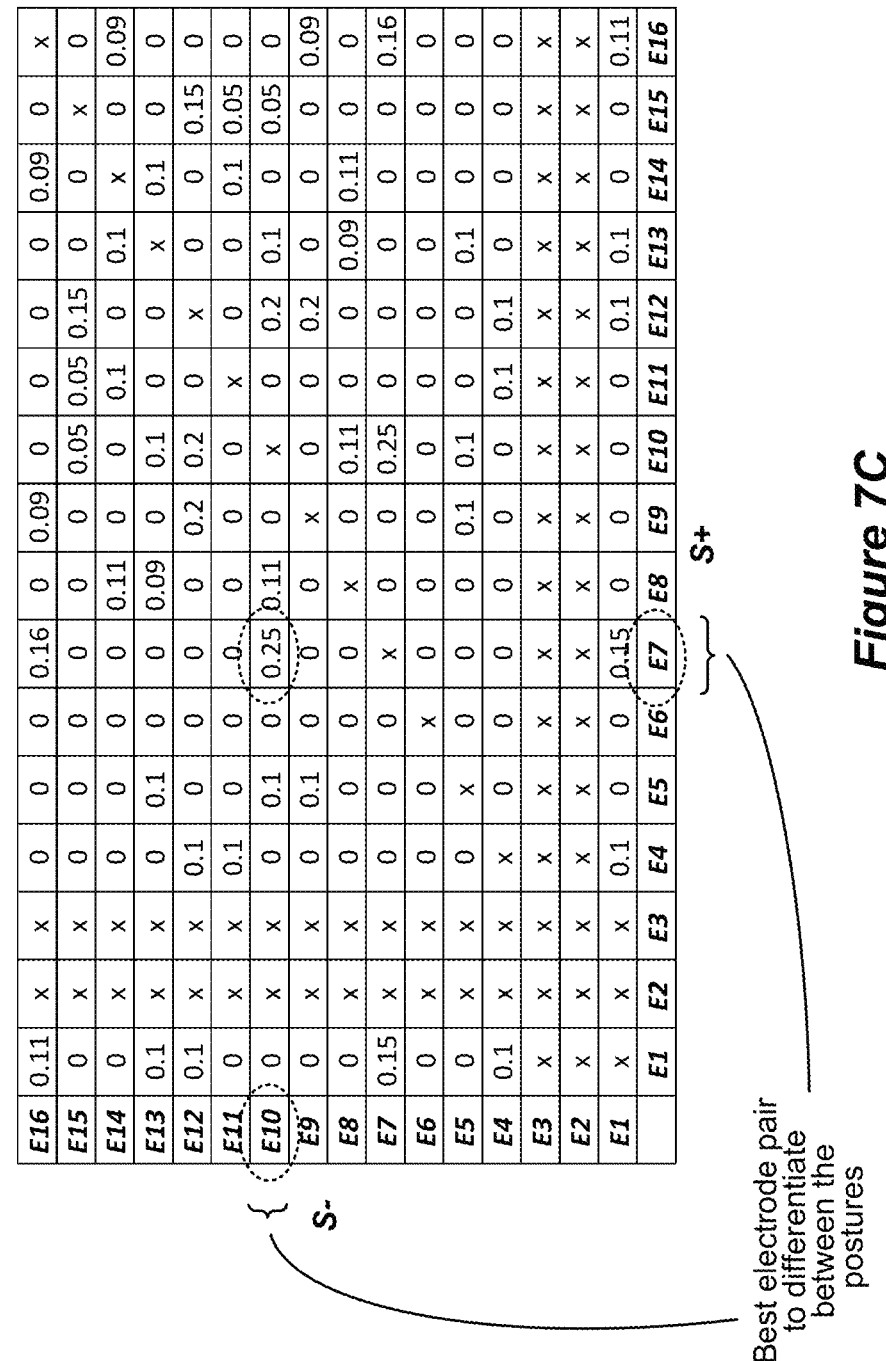
*Figure 7C*

150

*Feature Matrix 3 (max Stim Art amplitude):*
*Patient supine*

|     | E1   | E2 | E3 | E4   | E5   | E6   | E7   | E8   | E9   | E10  | E11  | E12  | E13  | E14  | E15  | E16  |
|-----|------|----|----|------|------|------|------|------|------|------|------|------|------|------|------|------|
| E16 | 1.39 | x  | x  | 1.39 | 0.69 | 0.2  | 0.1  | 0    | 0.49 | 0.29 | 0.29 | 0.49 | 0.1  | 0.09 | 0.1  | x    |
| E15 | 1.35 | x  | x  | 1.2  | 0.8  | 0.05 | 0    | 0.1  | 0.6  | 0.25 | 0.25 | 0.45 | 0.15 | 0    | x    | 0.1  |
| E14 | 1.3  | x  | x  | 1.3  | 0.6  | 0    | 0.05 | 0.09 | 0.5  | 0.2  | 0.2  | 0.6  | 0.1  | x    | 0    | 0.09 |
| E13 | 1.2  | x  | x  | 0.9  | 0.7  | 0.3  | 0.15 | 0.3  | 0.3  | 0.2  | 0.1  | 0.3  | x    | 0.1  | 0.15 | 0.1  |
| E12 | 0.8  | x  | x  | 0.8  | 0.2  | 0.4  | 0.45 | 0.4  | 0    | 0.2  | 0.2  | x    | 0.3  | 0.6  | 0.45 | 0.49 |
| E11 | 1    | x  | x  | 1.1  | 0.4  | 0.1  | 0.25 | 0.4  | 0.1  | 0    | x    | 0.2  | 0.1  | 0.2  | 0.25 | 0.29 |
| E10 | 0.9  | x  | x  | 1.1  | 0.4  | 0.2  | 0.25 | 0.29 | 0.2  | x    | 0    | 0.2  | 0.2  | 0.2  | 0.25 | 0.29 |
| E9  | 0.7  | x  | x  | 0.9  | 0.1  | 0.5  | 0.4  | 0.49 | x    | 0.2  | 0.1  | 0    | 0.3  | 0.5  | 0.6  | 0.49 |
| E8  | 1.39 | x  | x  | 1.39 | 0.69 | 0    | 0.04 | x    | 0.49 | 0.29 | 0.4  | 0.4  | 0.3  | 0.09 | 0.1  | 0    |
| E7  | 1.5  | x  | x  | 1.35 | 0.8  | 0.05 | x    | 0.04 | 0.4  | 0.25 | 0.25 | 0.45 | 0.15 | 0.05 | 0    | 0.1  |
| E6  | 1.3  | x  | x  | 1.4  | 0.6  | x    | 0.05 | 0    | 0.5  | 0.2  | 0.1  | 0.4  | 0.3  | 0    | 0.05 | 0.2  |
| E5  | 0.7  | x  | x  | 0.5  | x    | 0.6  | 0.8  | 0.69 | 0.1  | 0.4  | 0.4  | 0.2  | 0.7  | 0.6  | 0.8  | 0.69 |
| E4  | 0.1  | x  | x  | x    | 0.5  | 1.4  | 1.35 | 1.39 | 0.9  | 1.1  | 1.1  | 0.8  | 0.9  | 1.3  | 1.2  | 1.39 |
| E3  | x    | x  | x  | x    | x    | x    | x    | x    | x    | x    | x    | x    | x    | x    | x    | x    |
| E2  | x    | x  | x  | x    | x    | x    | x    | x    | x    | x    | x    | x    | x    | x    | x    | x    |
| E1  |      | x  | x  | 0.1  | 0.7  | 1.3  | 1.5  | 1.39 | 0.7  | 0.9  | 1    | 0.8  | 1.2  | 1.3  | 1.35 | 1.39 |

*Difference Matrix 2 (standing v. supine):*
*ABS(Feature Matrix 1 – Feature Matrix 3)*

*Difference Matrix 1 (standing v. sitting; Fig. 6C):*
*ABS(Feature Matrix 1 – Feature Matrix 2)*

*Difference Matrix 3 (sitting v. supine):*
*ABS(Feature Matrix 1 – Feature Matrix 2)*

Summed Difference Matrix:
Difference Matrix 1 + 2 + 3

E.g.:
0.16 from diff matrix 1
0.06 from diff matrix 2
0.1 from diff matrix 3

|      | E1   | E2 | E3 | E4  | E5  | E6   | E7   | E8   | E9   | E10  | E11  | E12  | E13  | E14  | E15  | E16  |
|------|------|----|----|-----|-----|------|------|------|------|------|------|------|------|------|------|------|
| E16  | 0.22 | x  | x  | 0   | 0   | 0.22 | 0.32 | 0    | 0.18 | 0    | 0    | 0    | 0.18 | 0.18 | 0.12 | x    |
| E15  | 0    | x  | x  | 0.3 | 0.3 | 0    | 0    | 0.12 | 0.3  | 0.1  | 0.1  | 0.3  | 0    | 0.1  | x    | 0.12 |
| E14  | 0    | x  | x  | 0   | 0   | 0    | 0    | 0.22 | 0.2  | 0.1  | 0.2  | 0.4  | 0.2  | x    | 0.1  | 0.18 |
| E13  | 0.2  | x  | x  | 0.6 | 0.6 | 0.4  | 0    | 0.4  | 0    | 0    | 0    | 0    | x    | 0.2  | 0    | 0.18 |
| E12  | 0.4  | x  | x  | 0.4 | 0   | 0    | 0    | 0.18 | 0.4  | 0.4  | 0    | x    | 0    | 0.4  | 0.3  | 0    |
| E11  | 0.2  | x  | x  | 0.2 | 0   | 0.2  | 0    | 0.22 | 0.2  | 0    | x    | 0    | 0    | 0.2  | 0.1  | 0    |
| E10  | 0.4  | x  | x  | 0   | 0.2 | 0    | 0.5  | 0.22 | 0    | x    | 0    | 0.4  | 0.4  | 0    | 0.1  | 0    |
| E9   | 0.4  | x  | x  | 0   | 0.4 | 0.2  | 0.1  | 0    | x    | 0    | 0.2  | 0.4  | 0    | 0.2  | 0.3  | 0.18 |
| E8   | 0    | x  | x  | 0   | 0   | 0.18 | 0    | x    | 0    | 0.22 | 0.22 | 0.18 | 0.4  | 0.22 | 0.12 | 0    |
| E7   | 0.6  | x  | x  | 0   | 0.3 | 0    | x    | 0    | 0.1  | 0.5  | 0    | 0    | 0    | 0    | 0    | 0.32 |
| E6   | 0    | x  | x  | 0.2 | 0   | x    | 0    | 0.18 | 0.2  | 0    | 0.2  | 0    | 0.4  | 0    | 0    | 0.22 |
| E5   | 0    | x  | x  | 0   | x   | 0    | 0.3  | 0    | 0.4  | 0.2  | 0    | 0    | 0.6  | 0    | 0.3  | 0    |
| E4   | 0.2  | x  | x  | x   | 0.4 | 0.2  | 0    | 0    | 0    | 0    | 0.2  | 0.4  | 0.6  | 0    | 0.3  | 0    |
| E3   | x    | x  | x  | x   | x   | x    | x    | x    | x    | x    | x    | x    | x    | x    | x    | x    |
| E2   | x    | x  | x  | x   | x   | x    | x    | x    | x    | x    | x    | x    | x    | x    | x    | x    |
| E1   | x    | x  | x  | 0.2 | 0   | 0    | 0.6  | 0    | 0.4  | 0.4  | 0.2  | 0.4  | 0.2  | 0    | 0    | 0.22 |

Feature Vector 1 (max Stim Art amplitude): Patient standing

| 3.9 | x | x | 3.9 | 3.2 | 2.6 | 2.55 | 2.51 | 3 | 2.8 | 2.8 | 3 | 2.7 | 2.6 | 2.55 | 2.51 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Feature Vector 2 (max Stim Art amplitude): Patient sitting

| 3.95 | x | x | 3.88 | 3.1 | 2.58 | 2.56 | 2.49 | 3 | 2.74 | 2.76 | 3.02 | 2.7 | 2.55 | 2.54 | 2.51 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Feature Vector 3 (max Stim Art amplitude): Patient supine

| 3.93 | x | x | 3.9 | 3.05 | 2.62 | 2.57 | 2.52 | 2.97 | 2.81 | 2.81 | 2.99 | 2.65 | 2.57 | 2.53 | 2.52 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Difference Vector 1 (standing v. sitting):
ABS(Feature Vector 1 – Feature Vector 2)

| 0.05 | x | x | 0.02 | 0.1 | 0.02 | 0.01 | 0.02 | 0 | 0.06 | 0.04 | 0.02 | 0 | 0.05 | 0.01 | 0 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Difference Vector 2 (standing v. supine):
ABS(Feature Vector 1 – Feature Vector 3)

| 0.03 | x | x | 0 | 0.15 | 0.02 | 0.02 | 0.01 | 0.03 | 0.01 | 0.01 | 0.01 | 0.05 | 0.03 | 0.02 | 0.01 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Difference Vector 3 (sitting v. supine):
ABS(Feature Vector 1 – Feature Vector 2)

| 0.02 | x | x | 0.02 | 0.05 | 0.04 | 0.01 | 0.03 | 0.03 | 0.07 | 0.05 | 0.03 | 0.05 | 0.02 | 0.01 | 0.01 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Summed Difference Vector:
Difference Vector 1 + 2 + 3

| 0.1 | x | x | 0.04 | 0.3 | 0.08 | 0.04 | 0.06 | 0.06 | 0.14 | 0.1 | 0.06 | 0.1 | 0.1 | 0.04 | 0.02 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Weighted Difference Vector:

| 0.002 | x | x | 0 | 0.015 | 0.002 | 4E-04 | 6E-04 | 0 | 0.001 | 0.001 | 6E-04 | 0 | 0 | 0 | 0 |
|---|---|---|---|---|---|---|---|---|---|---|---|---|---|---|---|
| E1 | E2 | E3 | E4 | E5 | E6 | E7 | E8 | E9 | E10 | E11 | E12 | E13 | E14 | E15 | E16 |

Best electrode to differentiate between the postures

*Figure 10*

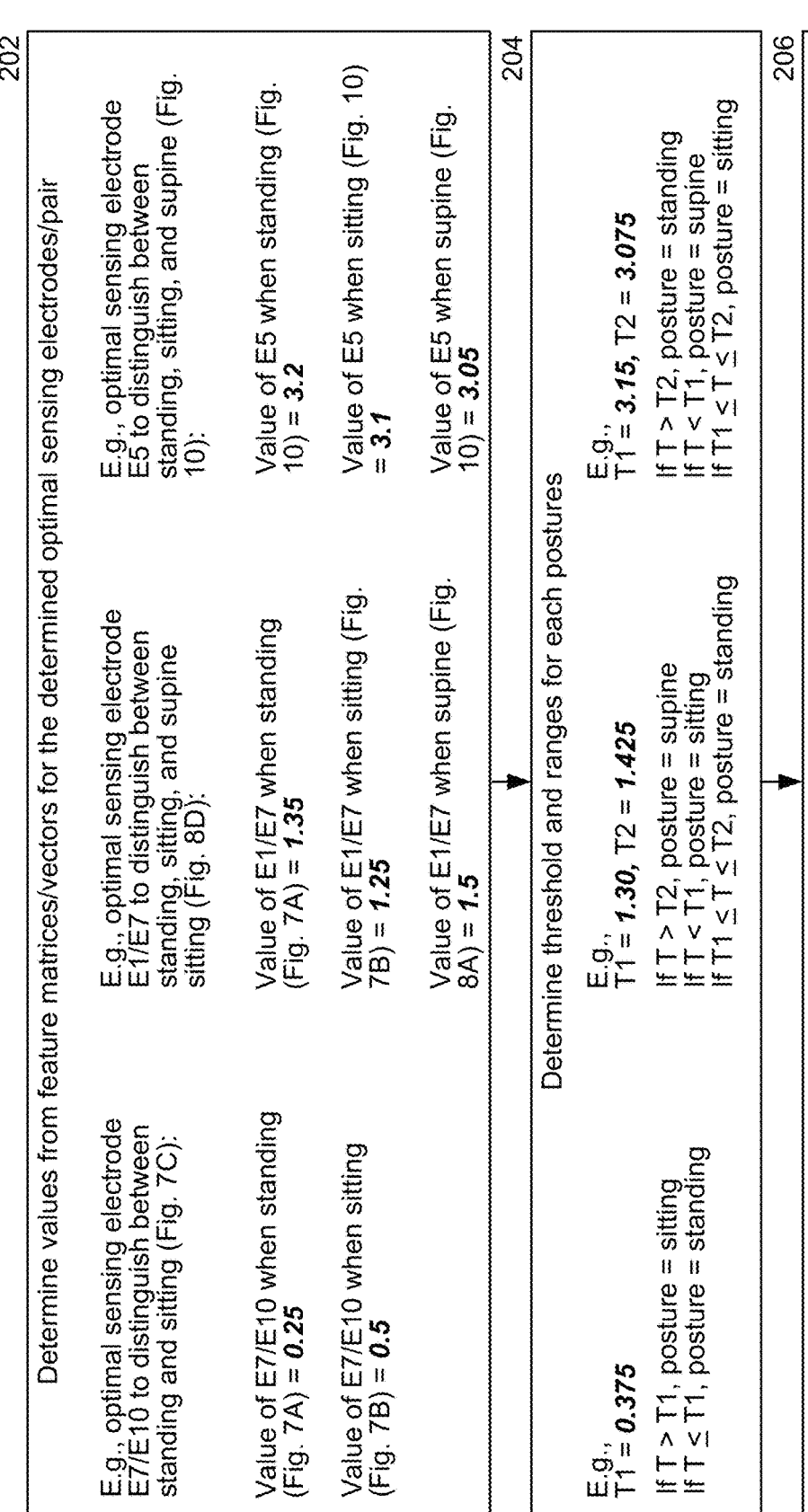

Posture threshold algorithm 200

202

Determine values from feature matrices/vectors for the determined optimal sensing electrodes/pair E.g., optimal sensing electrode E7/E10 to distinguish between standing and sitting (Fig. 7C):

Value of E7/E10 when standing (Fig. 7A) = 0.25

Value of E7/E10 when sitting (Fig. 7B) = 0.5

E.g., optimal sensing electrode E1/E7 to distinguish between standing, sitting, and supine (Fig. 8D):

Value of E1/E7 when standing (Fig. 7A) = 1.35

Value of E1/E7 when sitting (Fig. 7B) = 1.25

Value of E1/E7 when supine (Fig. 8A) = 1.5

E.g., optimal sensing electrode E5 to distinguish between standing, sitting, and supine (Fig. 10):

Value of E5 when standing (Fig. 10) = 3.2

Value of E5 when sitting (Fig. 10) = 3.1

Value of E5 when supine (Fig. 10) = 3.05

204

Determine threshold and ranges for each postures

E.g.,
T1 = 0.375

If T > T1, posture = sitting
If T ≤ T1, posture = standing

E.g.,
T1 = 1.30, T2 = 1.425

If T > T2, posture = supine
If T < T1, posture = sitting
If T1 ≤ T ≤ T2, posture = standing E.g.,
T1 = 3.15, T2 = 3.075

If T > T2, posture = standing
If T < T1, posture = supine
If T1 ≤ T ≤ T2, posture = sitting

206

Program the IPG with the determined threshold ranges for each posture to enable the IPG to make posture determinations

*Figure 12*

SELECTION OF SENSING ELECTRODES IN A SPINAL CORD STIMULATOR SYSTEM USING SENSED STIMULATION ARTIFACTS

CROSS REFERENCE TO RELATED APPLICATIONS

This is a continuation application of U.S. patent application Ser. No. 17/133,040, filed Dec. 23, 2020, which is a non-provisional application of U.S. Provisional Patent Application Ser. No. 62/970,448, filed Feb. 5, 2020. Priority is claimed to these applications, and they are incorporated herein by reference it their entireties.

FIELD OF THE INVENTION

This application relates to Implantable Medical Devices (IMDs), and more specifically sensing signals in an implantable stimulator device.

INTRODUCTION

Implantable neurostimulator devices are devices that generate and deliver electrical, light, thermal, magnetic, or ultrasound stimuli to body nerves and tissues for the therapy of various biological disorders, such as pacemakers to treat cardiac arrhythmia, defibrillators to treat cardiac fibrillation, cochlear stimulators to treat deafness, retinal stimulators to treat blindness, muscle stimulators to produce coordinated limb movement, spinal cord stimulators to treat chronic pain, cortical and deep brain stimulators to treat motor and psychological disorders, and other neural stimulators to treat urinary incontinence, sleep apnea, shoulder subluxation, etc. The description that follows will generally focus on the use of the invention within a Spinal Cord Stimulation (SCS) system using electrical stimuli, such as that disclosed in U.S. Pat. No. 6,516,227. However, the present invention may find applicability with any implantable neurostimulator device system, including systems utilizing other types of stimulation such us light including wavelength from 720 to 1250 nm.

An SCS system typically includes an Implantable Pulse Generator (IPG) 10 shown in FIG. 1. The IPG 10 includes a biocompatible device case 12 that holds the circuitry and a battery 14 for providing power for the IPG to function. The IPG 10 is coupled to tissue-stimulating electrodes 16 via one or more electrode leads that form an electrode array 17. For example, one or more percutaneous leads 15 can be used having ring-shaped or split-ring electrodes 16 carried on a flexible body 18. In another example, a paddle lead 19 provides electrodes 16 positioned on one of its generally flat surfaces. Lead wires 20 within the leads are coupled to the electrodes 16 and to proximal contacts 21 insertable into lead connectors 22 fixed in a header 23 on the IPG 10, which header can comprise an epoxy for example. Once inserted, the proximal contacts 21 connect to header contacts 24 within the lead connectors 22, which are in turn coupled by feedthrough pins 25 through a case feedthrough 26 to stimulation circuitry 28 within the case 12.

In the illustrated IPG 10, there are thirty-two electrodes (E1-E32), split between four percutaneous leads 15, or contained on a single paddle lead 19, and thus the header 23 may include a 2×2 array of eight-electrode lead connectors 22. However, the type and number of leads, and the number of electrodes, in an IPG is application-specific and therefore can vary. The conductive case 12 can also comprise an electrode (Ec). In a SCS application, the electrode lead(s)

are typically implanted in the spinal column proximate to the dura in a patient's spinal cord, preferably spanning left and right of the patient's spinal column. The proximal contacts 21 are tunneled through the patient's tissue to a distant location such as the buttocks where the IPG case 12 is implanted, at which point they are coupled to the lead connectors 22. In other IPG examples designed for implantation directly at a site requiring stimulation, the IPG can be lead-less, having electrodes 16 instead appearing on the body of the IPG 10 for contacting the patient's tissue. The IPG lead(s) can be integrated with and permanently connected to the IPG 10 in other solutions. The goal of SCS therapy is to provide electrical stimulation from the electrodes 16 to alleviate a patient's symptoms, such as chronic back pain.

IPG 10 can include an antenna 27a allowing it to communicate bi-directionally with a number of external devices used to program or monitor the IPG, such as a hand-held patient controller or a clinician's programmer, as described with respect to FIG. 4. Antenna 27a as shown comprises a conductive coil within the case 12, although the coil antenna 27a can also appear in the header 23. When antenna 27a is configured as a coil, communication with external devices preferably occurs using near-field magnetic induction. IPG 10 may also include a Radio-Frequency (RF) antenna 27b. In FIG. 1, RF antenna 27b is shown within the header 23, but it may also be within the case 12. RF antenna 27b may comprise a patch, slot, or wire, and may operate as a monopole or dipole. RF antenna 27b preferably communicates using far-field electromagnetic waves, and may operate in accordance with any number of known RF communication standards, such as Bluetooth, Zigbee, MICS, and the like.

Stimulation in IPG 10 is typically provided by pulses each of which may include a number of phases such as 30a and 30b, as shown in the example of FIG. 2A. Stimulation parameters typically include amplitude (current I, although a voltage amplitude V can also be used); frequency (F); pulse width (PW) of the pulses or of its individual phases; the electrodes 16 selected to provide the stimulation; and the polarity of such selected electrodes, i.e., whether they act as anodes that source current to the tissue or cathodes that sink current from the tissue. These and possibly other stimulation parameters taken together comprise a stimulation program that the stimulation circuitry 28 in the IPG 10 can execute to provide therapeutic stimulation to a patient.

In the example of FIG. 2A, electrode E4 has been selected as an anode (during its first phase 30a), and thus provides pulses which source a positive current of amplitude +I to the tissue. Electrode E5 has been selected as a cathode (again during first phase 30a), and thus provides pulses which sink a corresponding negative current of amplitude −I from the tissue. This is an example of bipolar stimulation, in which only two lead-based electrodes are used to provide stimulation to the tissue (one anode, one cathode). However, more than one electrode may be selected to act as an anode at a given time, and more than one electrode may be selected to act as a cathode at a given time. The case electrode Ec (12) can also be selected as an electrode, or current return, in what is known as monopolar situation.

IPG 10 as mentioned includes stimulation circuitry 28 to form prescribed stimulation at a patient's tissue. FIG. 3 shows an example of stimulation circuitry 28, which includes one or more current source circuits $40_i$ and one or more current sink circuits $42_i$. The sources and sinks $40_i$ and $42_i$ can comprise Digital-to-Analog converters (DACs), and may be referred to as PDACs $40_i$ and NDACs $42_i$ in accordance with the Positive (sourced, anodic) and Negative (sunk, cathodic) currents they respectively issue. In the example shown, a NDAC/PDAC $40_i/42_i$ pair is dedicated (hardwired) to a particular electrode node ei 39. Each electrode node ei 39 is connected to an electrode Ei 16 via a DC-blocking capacitor Ci 38, for the reasons explained below. The stimulation circuitry 28 in this example also supports selection of the conductive case 12 as an electrode (Ec 12), which case electrode is typically selected for monopolar stimulation. PDACs $40_i$ and NDACs $42_i$ can also comprise voltage sources.

Proper control of the PDACs $40_i$ and NDACs $42_i$ allows any of the electrodes 16 to act as anodes or cathodes to create a current through a patient's tissue, R, hopefully with good therapeutic effect. In the example shown (FIG. 2A), and during the first phase 30*a* in which electrodes E4 and E5 are selected as an anode and cathode respectively, PDAC $40_4$ and NDAC $42_5$ are activated and digitally programmed to produce the desired current, I, with the correct timing (e.g., in accordance with the prescribed frequency F and pulse width PWa). During the second phase 30*b* (PWb), PDAC 405 and NDAC 424 would be activated to reverse the polarity of the current. More than one anode electrode and more than one cathode electrode may be selected at one time, and thus current can flow through the tissue R between two or more of the electrodes 16.

Power for the stimulation circuitry 28 is provided by a compliance voltage VH. As described in further detail in U.S. Patent Application Publication 2013/0289665, the compliance voltage VH can be produced by a compliance voltage generator 29, which can comprise a circuit used to boost the battery 14's voltage (Vbat) to a voltage VH sufficient to drive the prescribed current I through the tissue R. The compliance voltage generator 29 may comprise an inductor-based boost converter as described in the '665 Publication, or can comprise a capacitor-based charge pump. Because the resistance of the tissue is variable, VH may also be variable, and can be as high as 18 Volts in one example.

Other stimulation circuitries 28 can also be used in the IPG 10. In an example not shown, a switching matrix can intervene between the one or more PDACs $40_i$ and the electrode nodes ei 39, and between the one or more NDACs $42_i$ and the electrode nodes. Switching matrices allow one or more of the PDACs or one or more of the NDACs to be connected to one or more anode or cathode electrode nodes at a given time. Various examples of stimulation circuitries can be found in U.S. Pat. Nos. 6,181,969, 8,606,362, 8,620, 436, and U.S. Patent Application Publications 2018/ 0071520 and 2019/0083796. Much of the stimulation circuitry 28 of FIG. 3, including the PDACs $40_i$ and NDACs $42_i$, the switch matrices (if present), and the electrode nodes ei 39 can be integrated on one or more Application Specific Integrated Circuits (ASICs), as described in U.S. Patent Application Publications 2012/0095529, 2012/0092031, and 2012/0095519, which are incorporated by reference. As explained in these references, ASIC(s) may also contain other circuitry useful in the IPG 10, such as telemetry circuitry (for interfacing off chip with telemetry antennas 27*a* and/or 27*b*), the compliance voltage generator 29, various measurement circuits, etc.

Also shown in FIG. 3 are DC-blocking capacitors Ci 38 placed in series in the electrode current paths between each of the electrode nodes ei 39 and the electrodes Ei 16 (including the case electrode Ec 12). The DC-blocking capacitors 38 act as a safety measure to prevent DC current injection into the patient, as could occur for example if there is a circuit fault in the stimulation circuitry 28. The DC-blocking capacitors 38 are typically provided off-chip (off of the ASIC(s)), and instead may be provided in or on a circuit board in the IPG 10 used to integrate its various components, as explained in U.S. Patent Application Publication 2015/ 0157861.

Although not shown, circuitry in the IPG 10 including the stimulation circuitry 28 can also be included in an External Trial Stimulator (ETS) device 80 (FIG. 4) which is used to mimic operation of the IPG during a trial period and prior to the IPG 10's implantation. An ETS 80 is typically used after the electrode array 17 has been implanted in the patient. The proximal ends of the leads in the electrode array 17 pass through an incision in the patient and are connected to the externally-worn ETS 80, thus allowing the ETS to provide stimulation to the patient during the trial period. The ETS 80 can include a coil antenna 82*a* or an RF antenna 82*b* for communicating with external devices, as described further below. Further details concerning an ETS device are described in U.S. Pat. No. 9,259,574 and U.S. Patent Application Publication 2019/0175915.

Referring again to FIG. 2A, the stimulation pulses as shown are biphasic, with each pulse at each electrode comprising a first phase 30*a* followed thereafter by a second phase 30*b* of opposite polarity. Biphasic pulses are useful to actively recover any charge that might be stored on capacitive elements in the electrode current paths, such as the DC-blocking capacitors 38, the electrode/tissue interface, or within the tissue itself. To recover all charge by the end of the second pulse phase 30*b* of each pulse (Vc4=Vc5=0V), the first and second phases 30*a* and 30*b* are preferably charged balanced at each electrode, with the phases comprising an equal amount of charge but of the opposite polarity. In the example shown, such charge balancing is achieved by using the same pulse width (PWa=PWb) and the same amplitude (|+I|=|−I|) for each of the pulse phases 30*a* and 30*b*. However, the pulse phases 30*a* and 30*b* may also be charged balance if the product of the amplitude and pulse widths of the two phases 30*a* and 30*b* are equal, as is known.

FIG. 3 shows that stimulation circuitry 28 can include passive recovery switches $41_i$, which are described further in U.S. Patent Application Publications 2018/0071527 and 2018/0140831. Passive recovery switches $41_i$ may be attached to each of the electrode nodes 39, and are used to passively recover any charge remaining on the DC-blocking capacitors Ci 38 after issuance of the second pulse phase 30*b*—i.e., to recover charge without actively driving a current using the DAC circuitry. Passive charge recovery can be prudent, because non-idealities in the stimulation circuitry 28 may lead to pulse phases 30*a* and 30*b* that are not perfectly charge balanced. Passive charge recovery typically occurs during at least a portion 30*c* (FIG. 2A) of the quiet periods between the pulses by closing passive recovery switches $41_i$. As shown in FIG. 3, the other end of the switches $41_i$ not coupled to the electrode nodes 39 are connected to a common reference voltage, which in this example comprises the voltage of the battery 14, Vbat, although another reference voltage could be used. As explained in the above-cited references, passive charge recovery tends to equilibrate the charge on the DC-blocking capacitors 38 and other capacitive elements by placing the capacitors in parallel between the reference voltage (Vbat) and the patient's tissue. Note that passive charge recovery is illustrated as small exponentially-decaying curves during 30*c* in FIG. 2A, which may be positive or negative depending on whether pulse phase 30*a* or 30*b* has a predominance of charge at a given electrode.

FIG. 4 shows various external devices that can wirelessly communicate with the IPG 10 and/or the ETS 80, including a patient, hand-held external controller 45, and a clinician programmer 50. Both of devices 45 and 50 can be used to wirelessly send a stimulation program to the IPG 10 or ETS 80—that is, to program their stimulation circuitries 28 and 44 to produce pulses with a desired shape and timing described earlier. Both devices 45 and 50 may also be used to adjust one or more stimulation parameters of a stimulation program that the IPG 10 or ETS 80 is currently executing. Devices 45 and 50 may also receive information from the IPG 10 or ETS 80, such as various status information, etc.

External controller 45 can be as described in U.S. Patent Application Publication 2015/0080982 for example, and may comprise either a dedicated controller configured to work with the IPG 10. External controller 45 may also comprise a general purpose mobile electronics device such as a mobile phone which has been programmed with a Medical Device Application (MDA) allowing it to work as a wireless controller for the IPG 10 or ETS 80, as described in U.S. Patent Application Publication 2015/0231402. External controller 45 includes a user interface, including means for entering commands (e.g., buttons or icons) and a display 46. The external controller 45's user interface enables a patient to adjust stimulation parameters, although it may have limited functionality when compared to the more-powerful clinician programmer 50, described shortly.

The external controller 45 can have one or more antennas capable of communicating with the IPG 10 and ETS 80. For example, the external controller 45 can have a near-field magnetic-induction coil antenna 47a capable of wirelessly communicating with the coil antenna 27a or 82a in the IPG 10 or ETS 80. The external controller 45 can also have a far-field RF antenna 47b capable of wirelessly communicating with the RF antenna 27b or 82b in the IPG 10 or ETS 80.

The external controller 45 can also have control circuitry 48 such as a microprocessor, microcomputer, an FPGA, other digital logic structures, etc., which is capable of executing instructions in an electronic device. Control circuitry 48 can for example receive patient adjustments to stimulation parameters, and create a stimulation program to be wirelessly transmitted to the IPG 10 or ETS 80.

Clinician programmer 50 is described further in U.S. Patent Application Publication 2015/0360038, and is only briefly explained here. The clinician programmer 50 can comprise a computing device 51, such as a desktop, laptop, or notebook computer, a tablet, a mobile smart phone, a Personal Data Assistant (PDA)-type mobile computing device, etc. In FIG. 4, computing device 51 is shown as a laptop computer that includes typical computer user interface means such as a screen 52, a mouse, a keyboard, speakers, a stylus, a printer, etc., not all of which are shown for convenience. Also shown in FIG. 4 are accessory devices for the clinician programmer 50 that are usually specific to its operation as a stimulation controller, such as a communication "wand" 54, and a joystick 58, which are coupleable to suitable ports on the computing device 51, such as USB ports 59 for example.

The antenna used in the clinician programmer 50 or its accessory devices to communicate with the IPG 10 or ETS 80 can depend on the type of antennas included in those devices. If the patient's IPG 10 or ETS 80 includes a coil antenna 27a or 82a, wand 54 can likewise include a coil antenna 56a to establish near-filed magnetic-induction communications at small distances. In this instance, the wand 54 may be affixed in close proximity to the patient, such as by placing the wand 54 in a belt or holster wearable by the patient and proximate to the patient's IPG 10 or ETS 80. If the IPG 10 or ETS 80 includes an RF antenna 27b or 82b, the wand 54, the computing device 51, or both, can likewise include an RF antenna 56b to establish communication with the IPG 10 or ETS 80 at larger distances. (Wand 54 may not be necessary in this circumstance). The clinician programmer 50 can also establish communication with other devices and networks, such as the Internet, either wirelessly or via a wired link provided at an Ethernet or network port.

To program stimulation programs or parameters for the IPG 10 or ETS 80, the clinician interfaces with a clinician programmer graphical user interface (GUI) 64 provided on the display 52 of the computing device 51. As one skilled in the art understands, the GUI 64 can be rendered by execution of clinician programmer software 66 on the computing device 51, which software may be stored in the device's non-volatile memory 68. One skilled in the art will additionally recognize that execution of the clinician programmer software 66 in the computing device 51 can be facilitated by controller circuitry 70 such as a microprocessor, microcomputer, an FPGA, other digital logic structures, etc., which is capable of executing programs in a computing device. In one example, controller circuitry 70 can include any of the i5 Core Processors, manufactured by Intel Corp. Such controller circuitry 70, in addition to executing the clinician programmer software 66 and rendering the GUI 64, can also enable communications via antennas 56a or 56b to communicate stimulation parameters chosen through the GUI 64 to the patient's IPG 10.

While GUI 64 is shown as operating in the clinician programmer 50, the user interface of the external controller 45 may provide similar functionality as the external controller 45 may have similar controller circuitry, software, etc.

SUMMARY

A method is disclosed for programming a stimulator device, the stimulator device comprising a plurality of electrodes configured to contact a patient's tissue. The method may comprise: (a) determining stimulation to be applied at at least two of the electrodes; (b) selecting a plurality of candidate pairs of the electrodes to act as sensing electrodes; (c) sensing a response to the stimulation at the candidate pairs with the patient in a posture; (d) determining a feature of the sensed response at each of the candidate pairs; (c) repeating steps (c) and (d) with the patient in at least one different posture; (f) comparing the determined features for each of the candidate pairs at the different postures to determine one or more optimal of the candidate pairs; and (g) programming the stimulator device with the one or more optimal pairs to be used for sensing with the stimulation.

In one example, the sensed response comprises a stimulation artifact, wherein the stimulation artifact comprises a signal formed by an electric field induced in the tissue by the stimulation. In one example, the sensed response comprises a neural response formed by recruitment of neural fibers in the tissue in response to the stimulation. In one example, the neural response comprises an evoked compound action potential. In one example, the plurality of candidate pairs selected in step (b) exclude the at least two electrodes to which the stimulation is to be applied. In one example, steps (a), (b), (f), and (g) are performed using an external device in communication with the stimulator device. In one example, the method is performed within the stimulator device. In one example, the sensed response is sensed differentially using both of the electrodes in each of the candidate pairs. In one example, there are two postures, and wherein the determined features for each of the candidate pairs at the two postures are compared by subtracting the determined features for each of the candidate pairs at the different postures. In one example, the one or more optimal pairs are determined as one or more candidate pairs having a largest difference after the subtraction. In one example, there are three or more postures. In one example, the determined features for each of the candidate pairs at the different postures are compared by (i) determining a number of difference matrices, wherein each difference matrix subtracts the determined features for each of the candidate pairs at two of the different postures. In one example, the determined features for each of the candidate pairs at the different postures are compared by (ii) summing the subtracted features in each of the difference matrices for each of the candidate pairs. In one example, the determined features for each of the candidate pairs at the different postures are compared by (iii) multiplying the sum by a minimum of the addends to form a weighted value for each of the candidate pairs. In one example, the one or more optimal pairs are determined as one or more candidate pairs having the largest weighted value. In one example, the stimulator device comprises a Spinal Cord Stimulator device. In one example, the method further comprises after step (g): (h) sensing a response to the stimulation at the determined one or more optimal pairs; (i) determining a feature of the response sensed at step (h); and (j) determining a posture of the patient using the feature determined at step (i). In one example, the method further comprises: (k) adjusting the stimulation in accordance with the determined posture. In one example, the method further comprises: (l) determining ranges for the feature, wherein each range corresponds to one of the postures, wherein the ranges are determined using the features as determined in step (d) at the different postures for the one or more optimal pairs. In one example, the method further comprises: (m) programming the stimulator device with the one or more ranges to enable the stimulator device to determine a posture of the patient.

An external device for programming a stimulator device is disclosed, the stimulator device comprising a plurality of electrodes configured to contact a patient's tissue, the external device comprising control circuitry configured to: (a) determine stimulation to be applied at at least two of the electrodes; (b) select a plurality of candidate pairs of the electrodes to act as sensing electrodes; (c) sense a response to the stimulation at the candidate pairs with the patient in a posture; (d) determine a feature of the sensed response at each of the candidate pairs; (e) repeat steps (c) and (d) with the patient in at least one different posture; (f) compare the determined features for each of the candidate pairs at the different postures to determine one or more optimal of the candidate pairs; and (g) program the stimulator device with the one or more optimal pairs to be used for sensing with the stimulation.

A non-transitory computer readable media is disclosed including instructions executable on an external device for programming a stimulator device, the stimulator device comprising a plurality of electrodes configured to contact a patient's tissue, wherein the instructions when executed are configured to: (a) determine stimulation to be applied at at least two of the electrodes; (b) select a plurality of candidate pairs of the electrodes to act as sensing electrodes; (c) sense a response to the stimulation at the candidate pairs with the patient in a posture; (d) determine a feature of the sensed response at each of the candidate pairs; (c) repeat steps (c)

and (d) with the patient in at least one different posture; (f) compare the determined features for each of the candidate pairs at the different postures to determine one or more optimal of the candidate pairs; and (g) program the stimulator device with the one or more optimal pairs to be used for sensing with the stimulation.

A method is disclosed for programming a stimulator device, the stimulator device comprising a plurality of electrodes configured to contact a patient's tissue. The method may comprise: (a) determining stimulation to be applied at at least two of the electrodes; (b) selecting a plurality of candidate electrodes from the plurality of electrodes to act as sensing electrodes; (c) sensing a response to the stimulation at the candidate electrodes with the patient in a posture; (d) determining a feature of the sensed response at each of the candidate electrodes; (c) repeating steps (c) and (d) with the patient in at least one different posture; (f) comparing the determined features for each of the candidate electrodes at the different postures to determine one or more optimal of the candidate electrodes; and (g) programming the stimulator device with the one or more optimal electrodes to be used for sensing with the stimulation.

In one example, the sensed response comprises a stimulation artifact, wherein the stimulation artifact comprises a signal formed by an electric field induced in the tissue by the stimulation. In one example, the sensed response comprises a neural response formed by recruitment of neural fibers in the tissue in response to the stimulation. In one example, the neural response comprises an evoked compound action potential. In one example, the plurality of candidate electrodes selected in step (b) exclude the at least two electrodes to which the stimulation is to be applied. In one example, steps (a), (b), (f), and (g) are performed using an external device in communication with the stimulator device. In one example, the method is performed within the stimulator device. In one example, the sensed response is sensed single-endedly using each of the candidate electrodes. In one example, there are two postures, and wherein the determined features for each of the candidate electrodes at the two postures are compared by subtracting the determined features for each of the candidate electrodes at the different postures. In one example, the one or more optimal electrodes are determined as one or more candidate electrodes having a largest difference after the subtraction. In one example, there are three or more postures. In one example, the determined features for each of the candidate electrodes at the different postures are compared by (i) determining a number of difference vectors, wherein each difference vector subtracts the determined features for each of the candidate electrodes at two of the different postures. In one example, the determined features for each of the candidate electrodes at the different postures are compared by (ii) summing the subtracted features in each of the difference vectors for each of the candidate electrodes. In one example, the determined features for each of the candidate electrodes at the different postures are compared by (iii) multiplying the sum by a minimum of the addends to form a weighted value for each of the candidate electrodes. In one example, the one or more optimal electrodes are determined as one or more candidate electrodes having the largest weighted value. In one example, the stimulator device comprises a Spinal Cord Stimulator device. In one example, the method further comprises after step (g): (h) sensing a response to the stimulation at the determined one or more optimal electrodes; (i) determining a feature of the response sensed at step (h); and (j) determining a posture of the patient using the feature determined at step (i). In one example, the method further comprises: (k) adjusting the stimulation in accordance with the determined posture. In one example, the method further comprises: (1) determining ranges for the feature, wherein each range corresponds to one of the postures, wherein the ranges are determined using the features as determined in step (d) at the different postures for the one or more optimal electrodes. In one example, the method further comprises: (m) programming the stimulator device with the one or more ranges to enable the stimulator device to determine a posture of the patient.

An external device for programming a stimulator device is disclosed, the stimulator device comprising a plurality of electrodes configured to contact a patient's tissue, the external device comprising: control circuitry configured to: (a) determine stimulation to be applied at at least two of the electrodes; (b) select a plurality of candidate electrodes from the plurality of electrodes to act as sensing electrodes; (c) sense a response to the stimulation at the candidate electrodes with the patient in a posture; (d) determine a feature of the sensed response at each of the candidate electrodes; (e) repeat steps (c) and (d) with the patient in at least one different posture; (f) compare the determined features for each of the candidate electrodes at the different postures to determine one or more optimal of the candidate electrodes; and (g) program the stimulator device with the one or more optimal electrodes to be used for sensing with the stimulation.

A non-transitory computer readable media is disclosed including instructions executable on an external device for programming a stimulator device, the stimulator device comprising a plurality of electrodes configured to contact a patient's tissue, wherein the instructions when executed are configured to: (a) determine stimulation to be applied at at least two of the electrodes; (b) select a plurality of candidate electrodes from the plurality of electrodes to act as sensing electrodes; (c) sense a response to the stimulation at the candidate electrodes with the patient in a posture; (d) determine a feature of the sensed response at each of the candidate electrodes; (e) repeat steps (c) and (d) with the patient in at least one different posture; (f) compare the determined features for each of the candidate electrodes at the different postures to determine one or more optimal of the candidate electrodes; and (g) program the stimulator device with the one or more optimal electrodes to be used for sensing with the stimulation.

The invention may also reside in the form of a programed external device (via its control circuitry) for carrying out the above methods, a programmed IPG or ETS (via its control circuitry) for carrying out the above methods, a system including a programmed external device and IPG or ETS for carrying out the above methods, or as a computer readable media for carrying out the above methods stored in an external device or IPG or ETS.

BRIEF DESCRIPTION OF THE DRAWINGS

FIG. 4 shows external devices able to communicate with the IPG, in accordance with the prior art.

signal which may include Evoked Compound Action Potentials (ECAPs) and stimulation artifacts.

Figure 6:
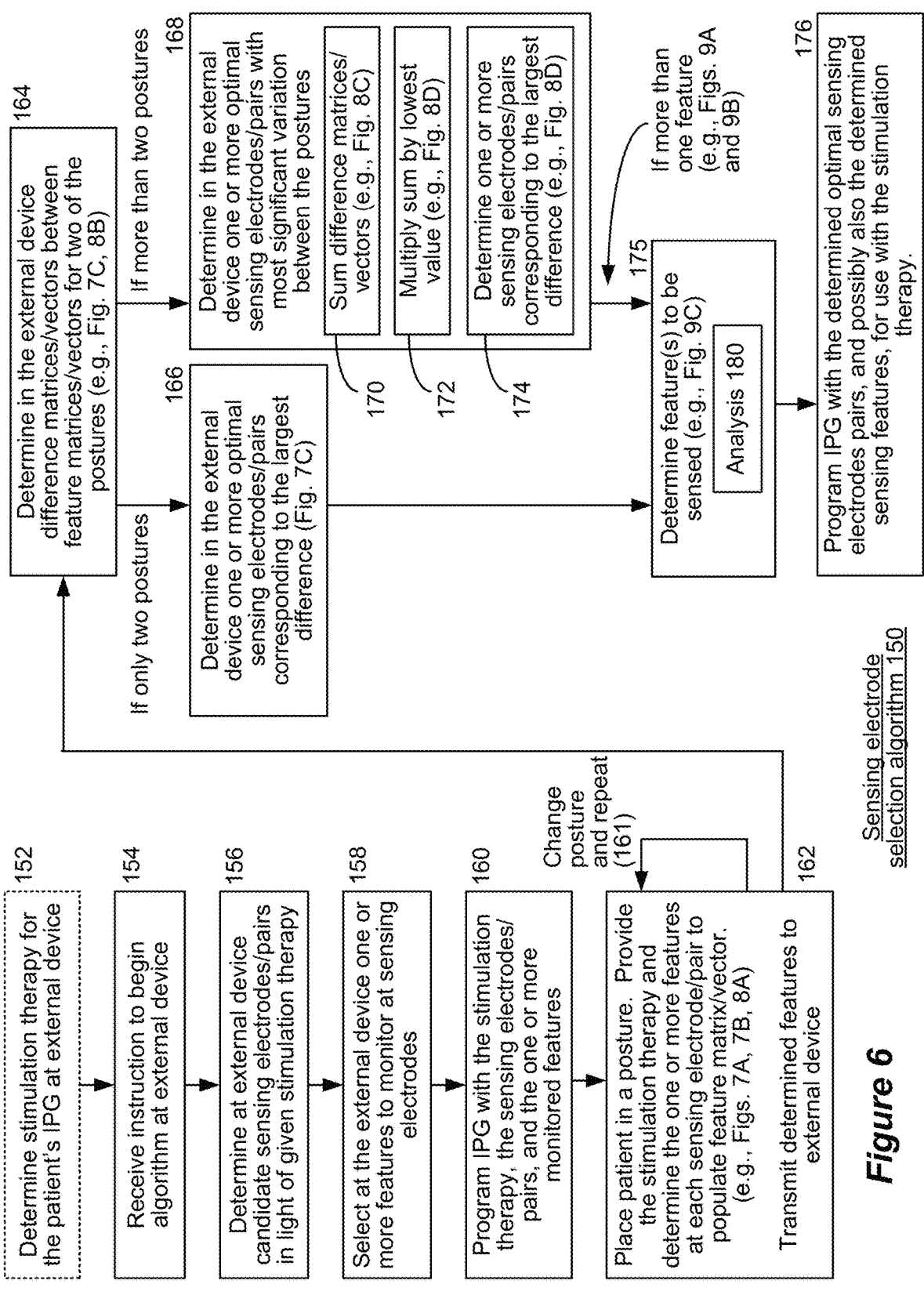

FIG. 6 shows a flow chart describing a sensing electrode selection algorithm operable to determine optimal sensing electrodes given a particular stimulation therapy for a patient, which is preferably implemented in an external device in communication with the patient's IPG.

Figure 7A:
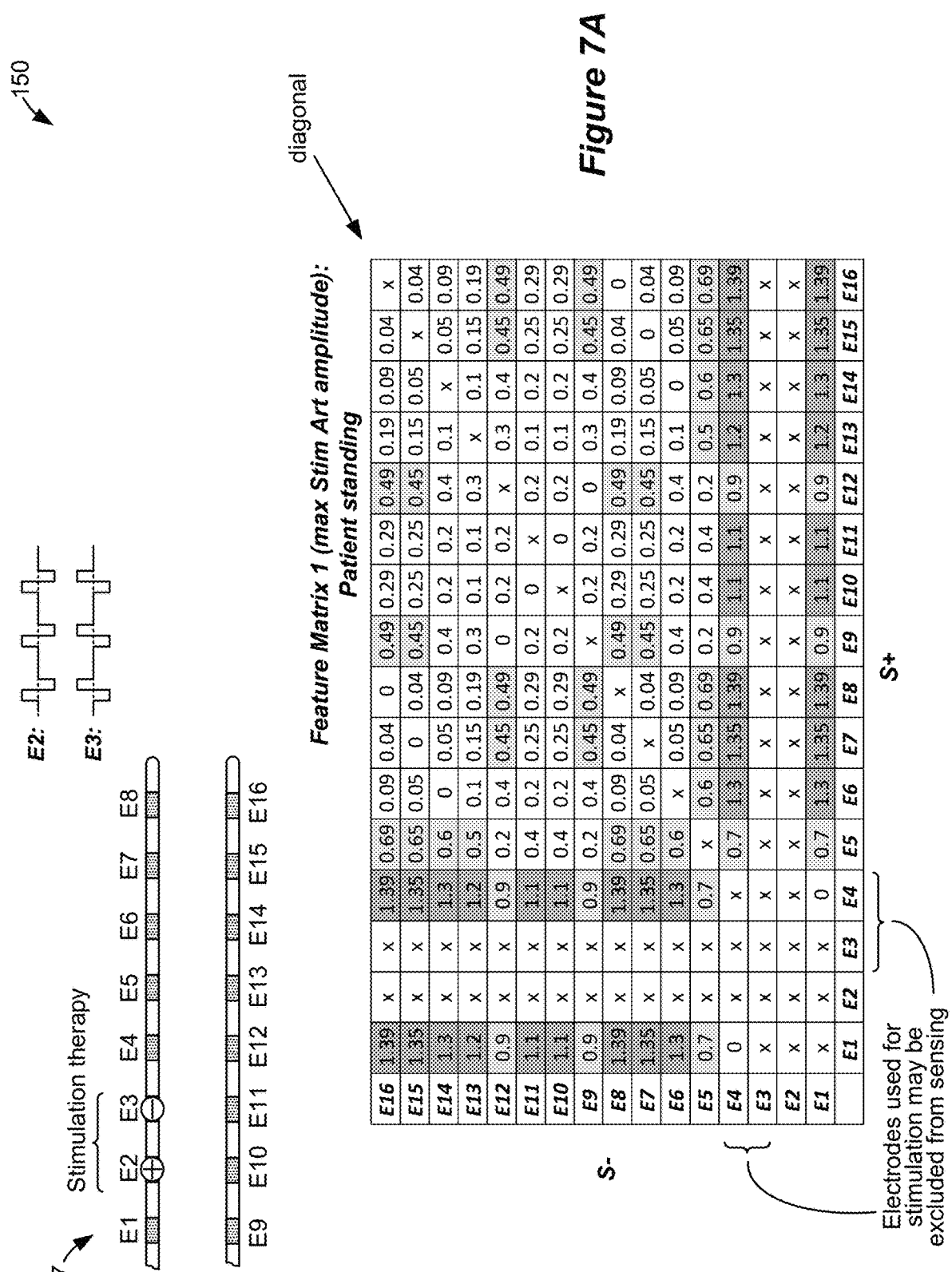

FIG. 7A shows a step in the sensing electrode sensing algorithm, and shows a feature matrix showing sensed stimulation artifacts features with the patient in a posture and using different sensing electrodes in the electrode array.

Figure 7B:

FIG. 7B shows a feature matrix similar to FIG. 6B, but with the patient in a different posture.

FIG. 7C shows a difference matrix subtracting the features in the matrices of FIGS. 7A and 7B, which allows the sensing electrode selection algorithm to determine optimal sensing electrodes that differentiate between the postures given the stimulation therapy.

FIG. 8A shows a feature matrix similar to FIGS. 7A and 7B, but with the patient in a third posture.

Figure 8B:
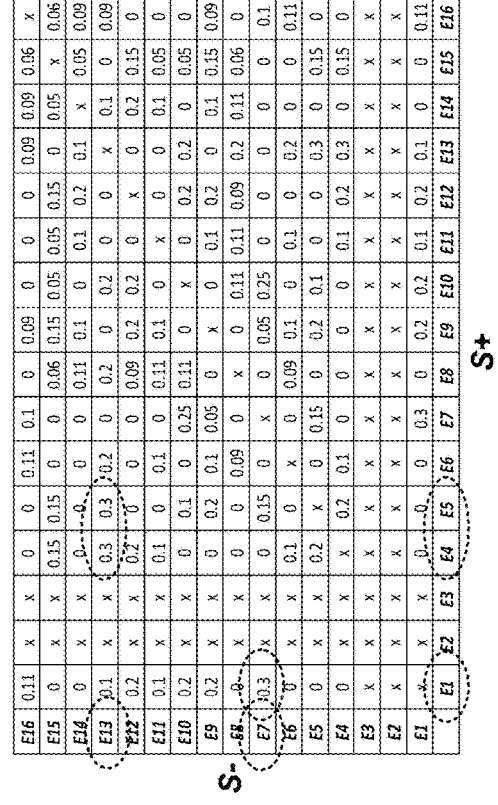

FIG. 8B shows difference matrices between two of the three postures represented by the feature matrices of FIGS. 7A, 7B, and 8A.

Figure 8C:
Figure 8D:
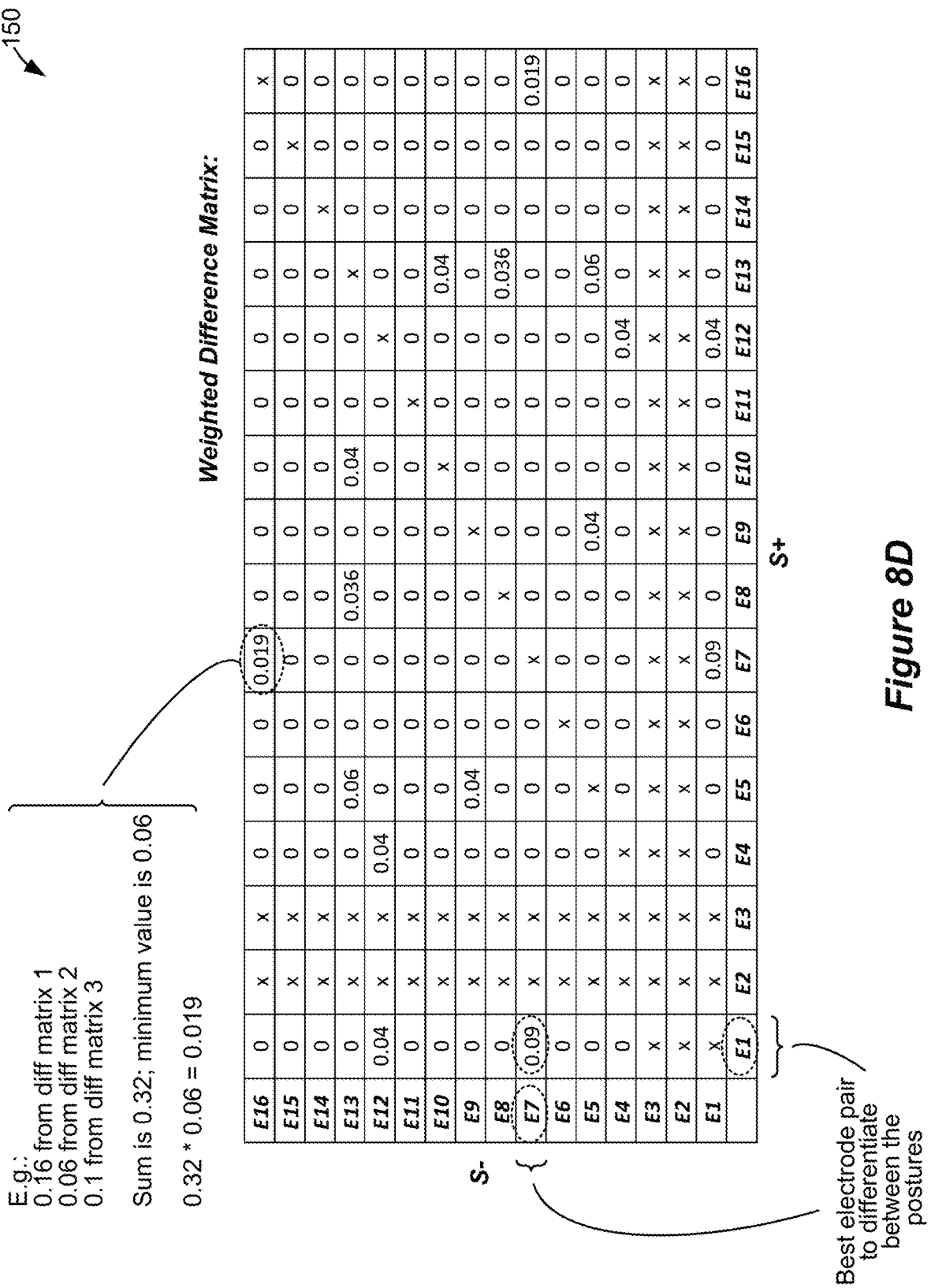

FIG. 8C shows summing of the difference matrices of FIG. 8B, and FIG. 8D shows multiplying the elements of the summed difference matrix by minimum values comprising the sum for each element, which allows the sensing electrode selection algorithm to determine optimal sensing electrodes to differentiate between the three postures given the stimulation therapy.

Figure 9A:
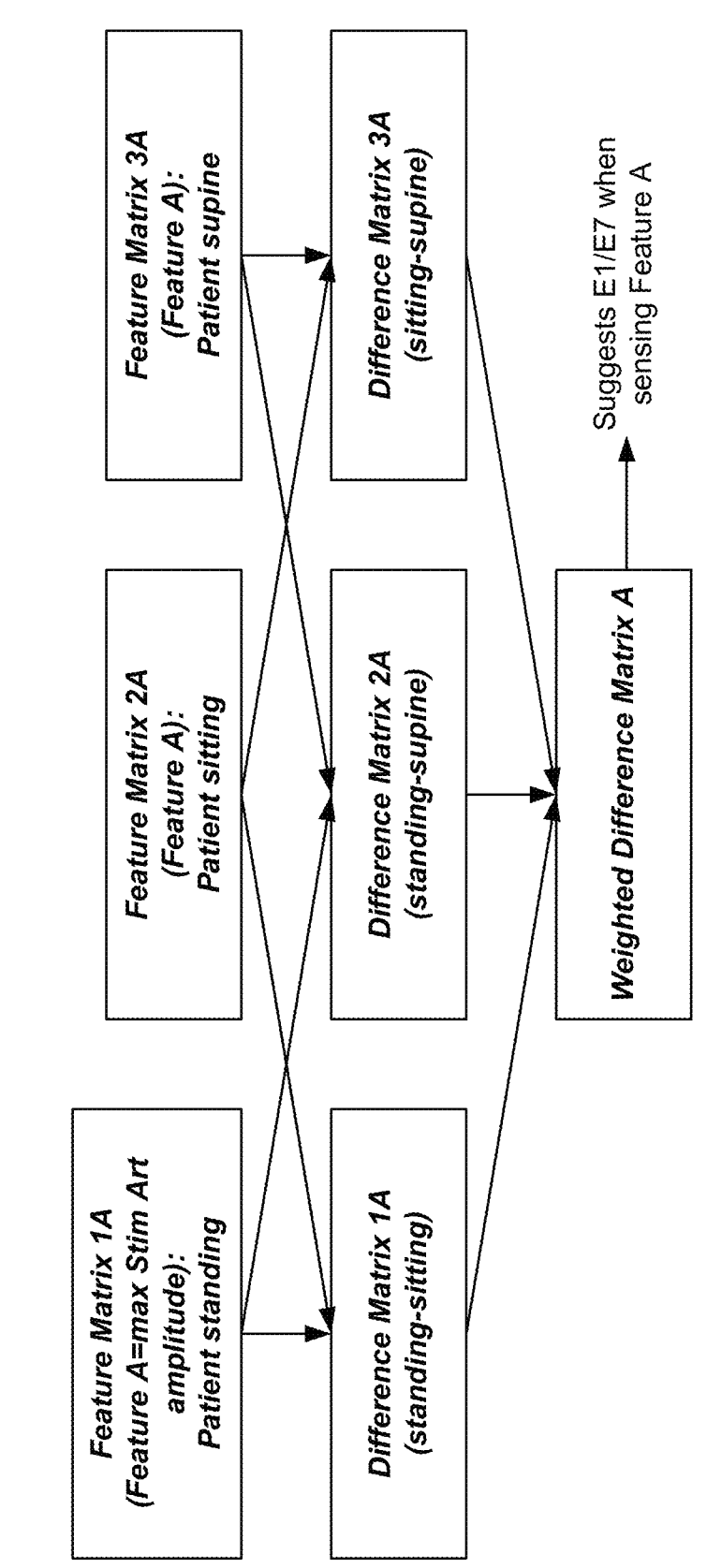
Figures 9B, 9C:
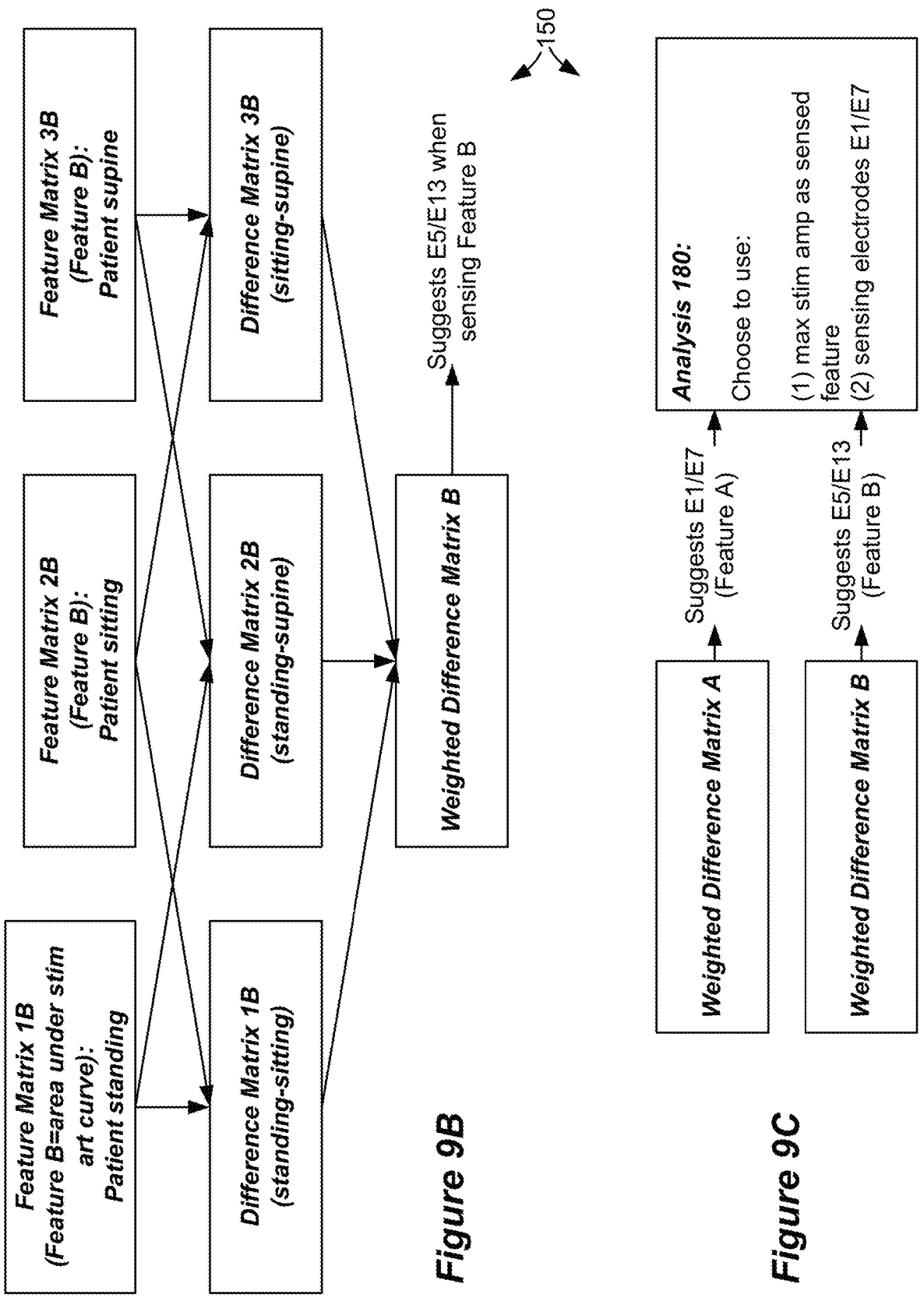

FIGS. 9A-9C show operation of the sensing electrode section algorithm where two features of stimulation artifacts are sensed, thus allowing the algorithm to additionally determine a stimulation artifact feature to be sensed.

FIG. 10 shows use of the sensing electrode selection algorithm when single-ended sensing is used, which changes the matrices described above to vectors.

Figure 11:
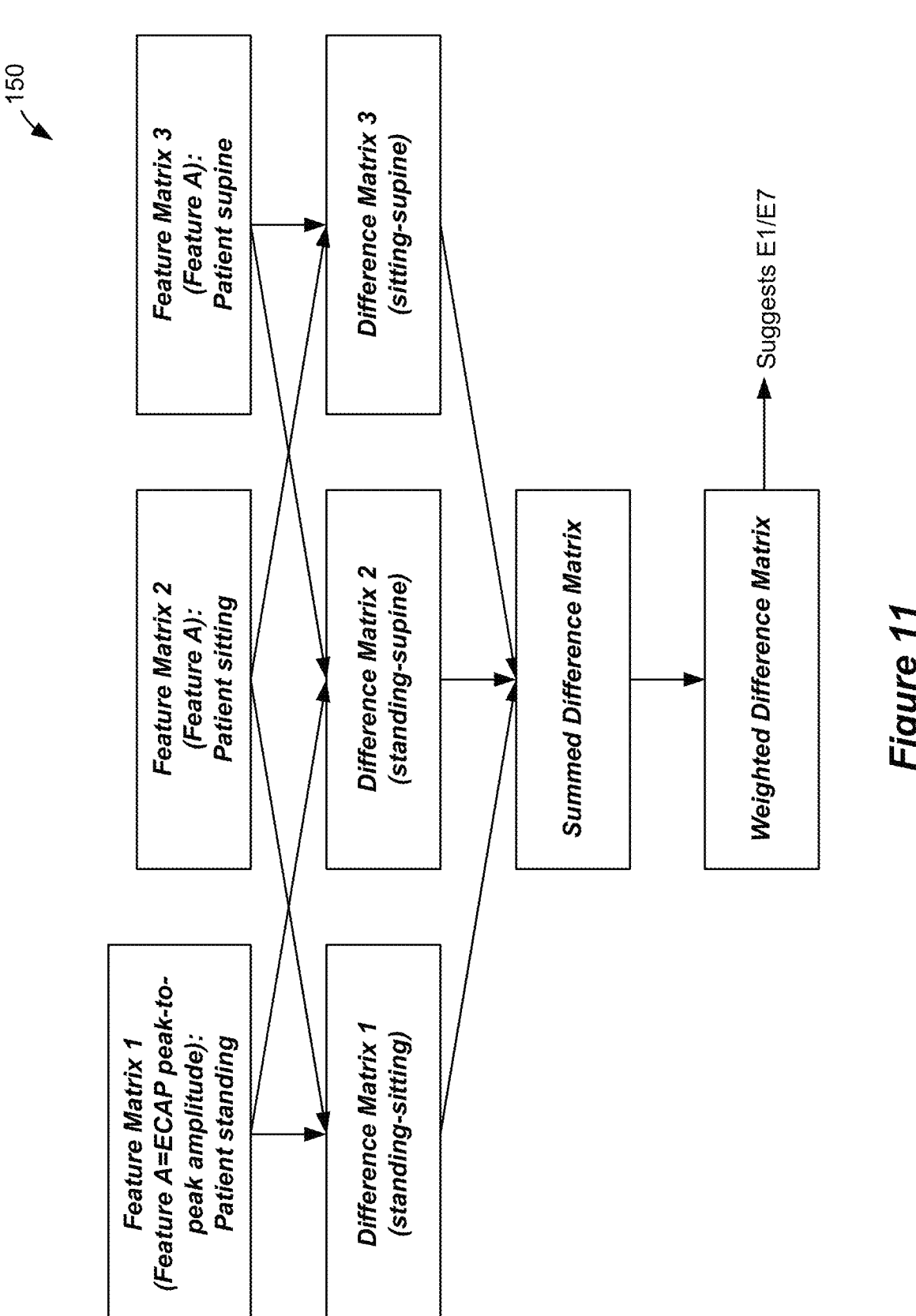

FIG. 11 shows use of the sensing electrode selection algorithm as described above, but by sensing of different ESG features, namely Evoked Compound Action Potential (ECAP) features, rather than stimulation artifact features.

FIG. 12 shows a posture threshold algorithm which can use the data from the sensing electrode selection algorithm to associate the tested postures with feature threshold ranges.

Figure 13:
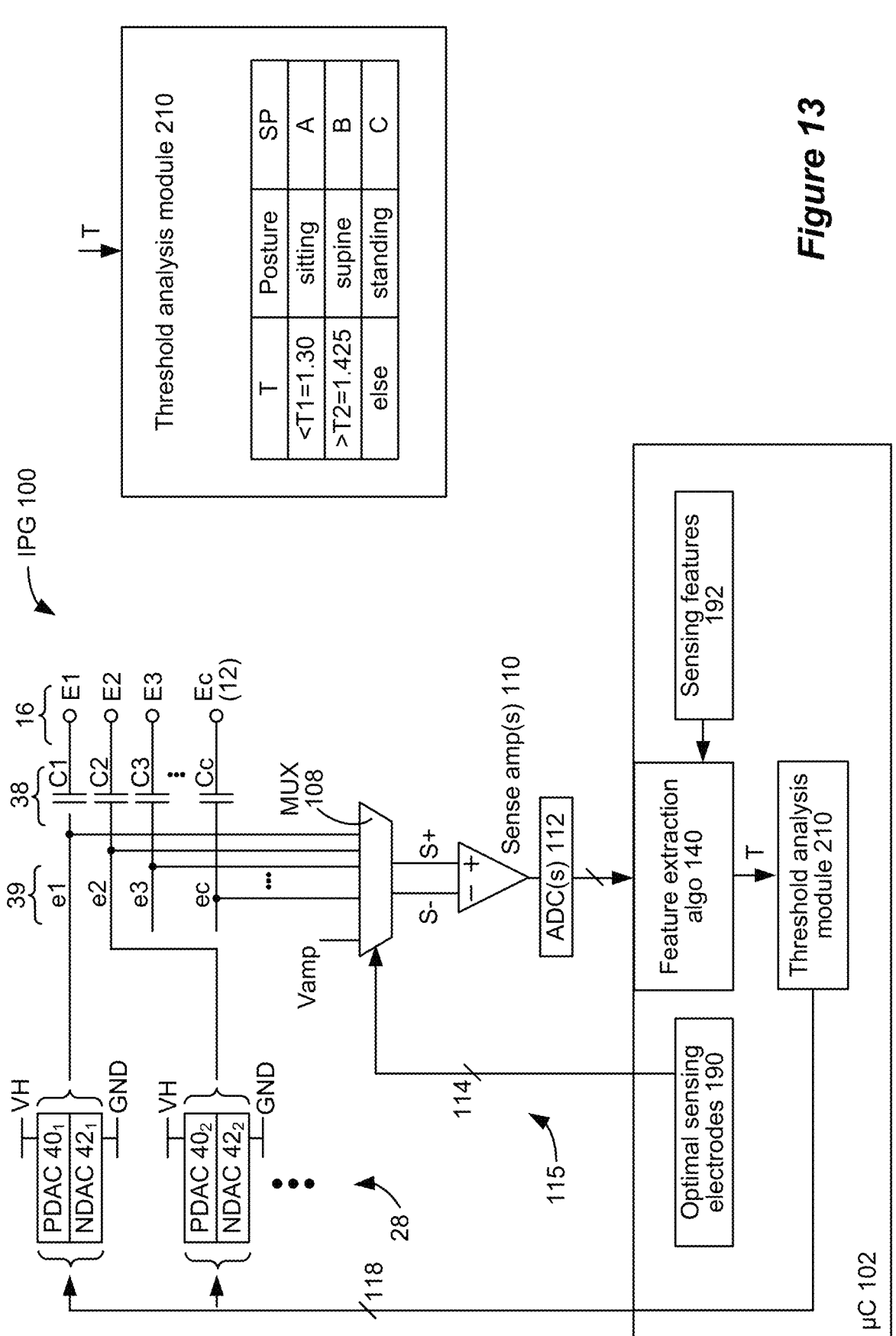

FIG. 13 shows the programming of the IPG in response to operation of the sensing electrode selection algorithm and the posture threshold algorithm.

DETAILED DESCRIPTION

Figure 5:
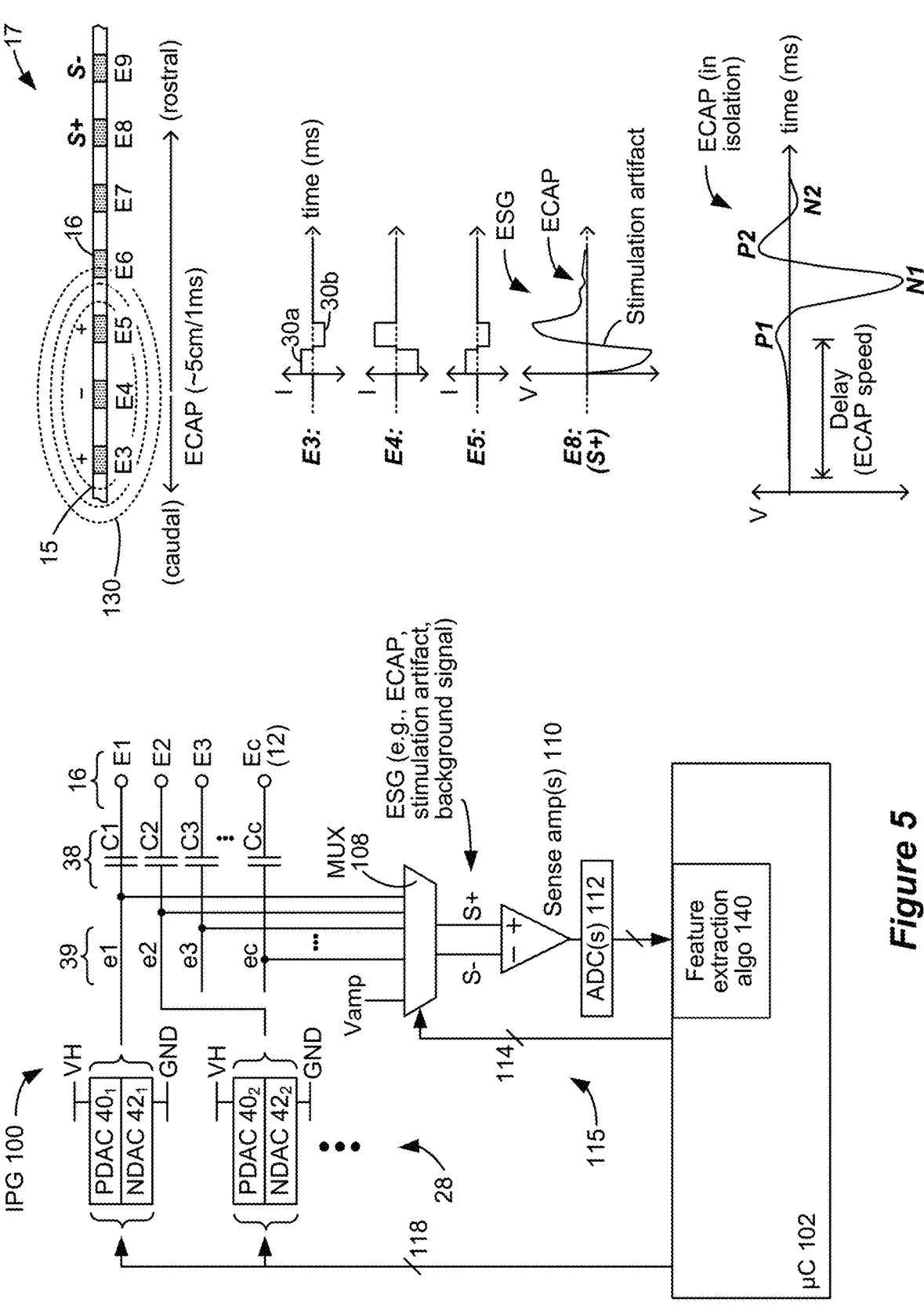
FIG. 5 shows an improved IPG having stimulation capability and the ability to sense an ElectroSpinoGram (ESG)

An increasingly interesting development in pulse generator systems, and in Spinal Cord Stimulator (SCS) pulse generator systems specifically, is the addition of sensing capability to complement the stimulation that such systems provide. FIG. 5 shows an IPG 100 that includes stimulation and sensing functionality. (An ETS as described earlier could also include the circuitry shown in FIG. 5, but this disclosure focuses on description in an IPG for simplicity).

For example, it can be beneficial to sense a neural response in neural tissue that has received stimulation from the IPG 100. One such neural response is an Evoked Compound Action Potential (ECAP). An ECAP comprises a cumulative response provided by neural fibers that are recruited by the stimulation, and essentially comprises the sum of the action potentials of recruited neural elements (ganglia or fibers) when they "fire." An ECAP is shown in isolation in FIG. 5, and comprises a number of peaks that are conventionally labeled with P for positive peaks and N for negative peaks, with P1 comprising a first positive peak, N1 a first negative peak, P2 a second positive peak, and so on. Note that not all ECAPs will have the exact shape and number of peaks as illustrated in FIG. 5, because an ECAP's shape is a function of the number and types of neural elements that are recruited and that are involved in its conduction. An ECAP is generally a small signal, and may have a peak-to-peak amplitude on the order of hundreds of micro Volts or more.

FIG. 5 also shows an electrode array 17 comprising (in this example) a single percutaneous lead 15, and shows use of electrodes E3, E4 and E5 to produce pulses in a tripolar mode of stimulation, with (during the first phase 30a) E3 and E5 comprising anodes and E4 a cathode. Other electrode arrangements (e.g., bipoles, etc.) could be used as well. Such stimulation produces an electric field 130 in a volume of the patient's tissue centered around the selected electrodes. Some of the neural fibers within the electric field 130 will be recruited and fire, particularly those proximate to the cathodic electrode E4, forming ECAPs which can travel both rostrally toward the brain and caudally away from the brain. The ECAPs pass through the spinal cord by neural conduction with a speed which is dependent on the neural fibers involved in the conduction. In one example, the ECAP may move at a speed of about 5 cm/1 ms. U.S. Patent Application Publication 2020/0155019 describes a lead that can be useful in the detection of ECAPs.

ECAPs can be sensed at one or more sensing electrodes which can be selected from the electrodes 16 in the electrode array 17. Sensing preferably occurs differentially, with one electrode (e.g., S+, E8) used for sensing and another (e.g., S−, E9) used as a sensing reference. This could also be flipped, with E8 providing the reference (S−) for sensing at electrode E9 (S+). Although not shown, the case electrode Ec (12) can also be used as a sensing reference electrode S−. Sensing reference S− could also comprise a fixed voltage provided by the IPG 100 (e.g., Vamp, discussed below), such as ground, in which case sensing would be said to be single-ended instead of differential.

The waveform appearing at sensing electrode E8 (S+) is shown in FIG. 5, which includes a stimulation artifact as well as an ECAP. The stimulation artifact comprises a voltage that is formed in the tissue as a result of the stimulation, i.e., as a result of the electric field 130 that the stimulation creates in the tissue. As described in U.S. Patent Application Publication 2019/0299006, the voltage formed in the tissue in response to the stimulation can vary between ground and the compliance voltage VH used to power the DACs, and so the stimulation artifact can be on the order of Volts, and therefore significantly higher than the magnitude of stimulation-induced ECAPs. Generally speaking, the waveform sensed at the sensing electrodes may be referred to as an ElectroSpinoGram (ESG) signal, which comprises the ECAP, the stimulation artifact, and other background signals that may be produced by neural tissue even absent stimulation. Realize that the ESG signal as shown at the sensing electrode S+ in FIG. 5 is idealized. The figures in PCT (Int'l) Patent Application Publication WO 2020/251899 show actual recorded ESG traces.

The magnitudes of the stimulation artifact and the ECAP at the sensing electrodes S+ and S− are dependent on many factors, such as the strength of the stimulation, the distance of sensing electrodes from the stimulation, and the distance of the sensing electrodes (S+ and S−) from each other. ECAPs tend to decrease in magnitude at increasing stimulation-to-sensing distances because they disperse in neural tissue as they travel. Stimulation artifacts also decrease in magnitude at increasing stimulation-to-sensing distances because the electric field 130 is weaker at further distances. Note that the stimulation artifact is also generally larger during the provision of the pulses, although it may still be present even after the pulse (i.e., the last phase 30b of the pulse) has ceased, due to the capacitive nature of the tissue or the capacitive nature of the driving circuitry (i.e., the DACs). As a result, the electric field 130 may not dissipate immediately upon cessation of the pulse.

It can be useful to sense in the IPG 100 features of either or both of the ECAPs or stimulation artifact contained within the sensed ESG signal, because such features can be used to useful ends. For example, sensed ECAP features, such as those discussed further below, can be used to adjust the stimulation the IPG 100 provides. Sec, e.g., U.S. Pat. No. 10,406,368; U.S. Patent Application Publications 2019/0099602, 2019/0209844, 2020/0147393, and 2019/0070418. ECAP assessment can also be used to infer the types of neural elements or fibers that are recruited, which can in turn be used to adjust the stimulation to selectively stimulate such elements. See, e.g., U.S. Patent Application Publication 2019/0275331. Assessments of ECAP features can also be used to determine cardiovascular effects, such as a patient's heart rate. See, e.g., U.S. Patent Application Publication 2019/0290900. To the extent one wishes to assess features of an ECAP that are obscured by a stimulation artifact, U.S. Patent Application Publication 2019/0366094 discloses techniques that can used to extract ECAP features from the ESG signal. As discussed in some of these references, detected ECAPs can also be dependent on a patient's posture or activity, and therefore assessment of ECAP features can be used to infer a patient's posture, which may then in turn be used to adjust the stimulation that the IPG 100 provides.

It can also be useful to detect features of stimulation artifacts in their own right. For example, PCT (Int'l) Patent Application Publication WO 2020/251899 describes that sensed stimulation artifacts features, discussed further below, can be useful to determining patent posture or activity, which again may then in turn be used to adjust the stimulation that the IPG 100 provides.

FIG. 5 shows further details of the circuitry in an IPG 100 that can provide stimulation and sensing of an ElectroSpinoGram (ESG) signal. The IPG 100 includes control circuitry 102, which may comprise a microcontroller, such as Part Number MSP430, manufactured by Texas Instruments, Inc., which is described in data sheets at http://www.ti.com/microcontrollers/msp430-ultra-low-power-mcus/overview.html, which are incorporated herein by reference. Other types of controller circuitry may be used in lieu of a microcontroller as well, such as microprocessors, FPGAs, DSPs, or combinations of these, etc. Control circuitry 102 may also be formed in whole or in part in one or more Application Specific Integrated Circuits (ASICs), such as those described and incorporated earlier.

Figure 3:
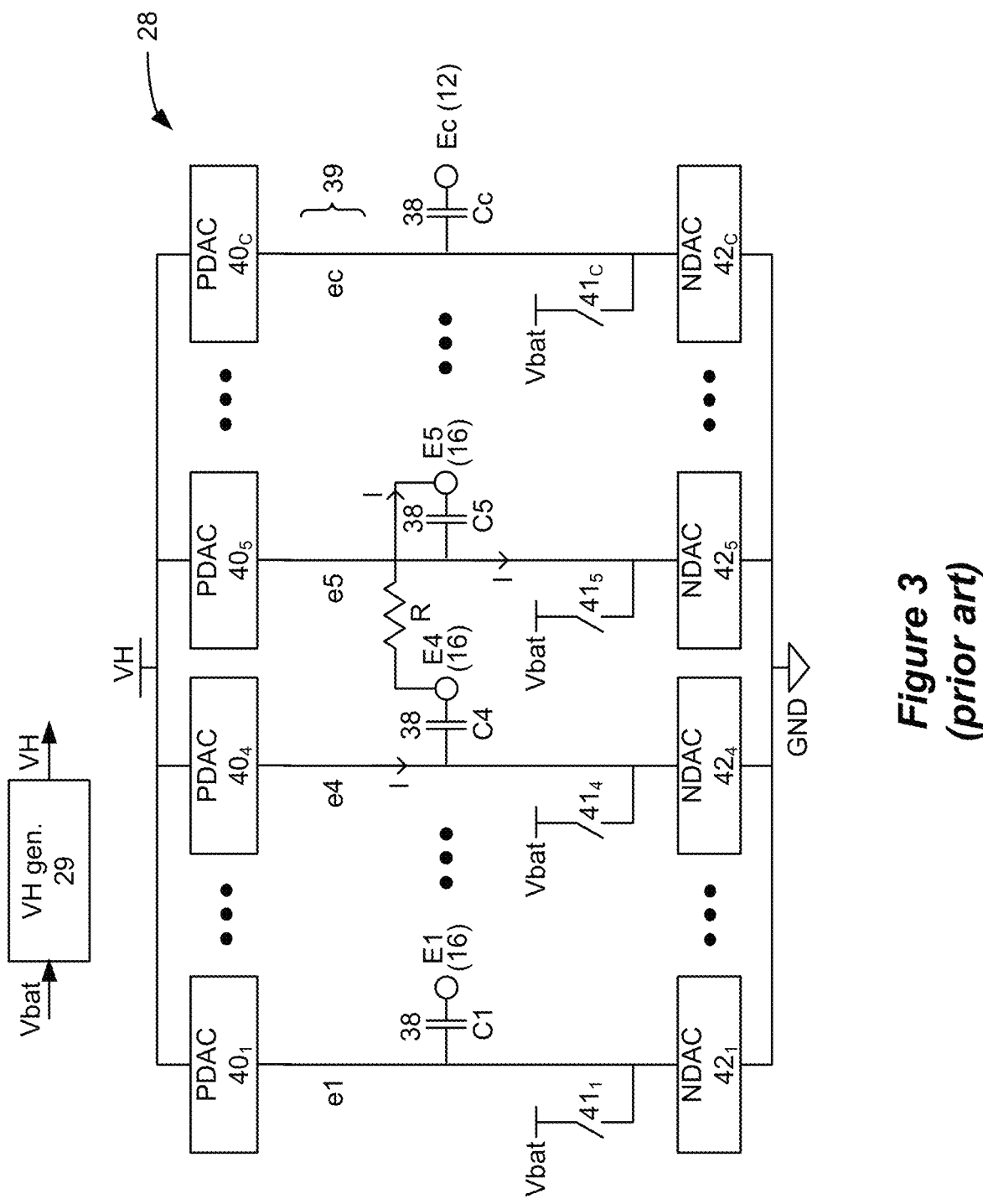
FIG. 3 shows stimulation circuitry useable in the IPG, in accordance with the prior art.

The IPG 100 also includes stimulation circuitry 28 to produce stimulation at the electrodes 16, which may comprise the stimulation circuitry 28 shown earlier (FIG. 3). A bus 118 provides digital control signals from the control circuitry 102 (and possibly from an feature extraction algorithm 140, described below) to one or more PDACs 40; or NDACs 42; to produce currents or voltages of prescribed amplitudes (I) for the stimulation pulses, and with the correct timing (PW, F) at selected electrodes. As noted earlier, the DACs can be powered between a compliance voltage VH and ground. As also noted earlier, but not shown in FIG. 5, switch matrices could intervene between the PDACs and the electrode nodes 39, and between the NDACs and the electrode nodes 39, to route their outputs to one or more of the electrodes, including the conductive case electrode 12 (Ec). Control signals for switch matrices, if present, may also be carried by bus 118. Notice that the current paths to the electrodes 16 include the DC-blocking capacitors 38 described earlier, which provide safety by preventing the inadvertent supply of DC current to an electrode and to a patient's tissue. Passive recovery switches 41$_i$ (FIG. 3) could also be present, but are not shown in FIG. 5 for simplicity.

IPG 100 also includes sensing circuitry 115, and one or more of the electrodes 16 can be used to sense signals the ESG signal. In this regard, each electrode node 39 is further coupleable to a sense amp circuit 110. Under control by bus 114, a multiplexer 108 can select one or more electrodes to operate as sensing electrodes (S+, S−) by coupling the electrode(s) to the sense amps circuit 110 at a given time, as explained further below. Although only one multiplexer 108 and sense amp circuit 110 are shown in FIG. 5, there could be more than one, and there may be at least two—one used to selected sensing electrode S+ and one used to select sensing reference S−. For example, there can be four multiplexer 108/sense amp circuit 110 pairs each operable within one of four timing channels supported by the IPG 100 to provide stimulation. The sensed signals output by the sense amp circuitry are preferably converted to digital signals by one or more Analog-to-Digital converters (ADC(s)) 112, which may sample the output of the sense amp circuit 110 at 50 kHz for example. The ADC(s) 112 may also reside within the control circuitry 102, particularly if the control circuitry 102 has A/D inputs. Multiplexer 108 can also provide a fixed reference voltage, Vamp, to the sense amp circuit 110, as is useful in a single-ended sensing mode (i.e., to set S− to Vamp).

So as not to bypass the safety provided by the DC-blocking capacitors 38, the inputs to the sense amp circuitry 110 are preferably taken from the electrode nodes 39. However, the DC-blocking capacitors 38 will pass AC signal components (while blocking DC components), and thus AC components within the ESG signals being sensed at the electrodes 16 (such as the ECAP and stimulation artifact) will still readily be sensed by the sense amp circuitry 110. In other examples, signals may be sensed directly at the electrodes 16 without passage through intervening capacitors 38.

As noted above, it is preferred to sense an ESG signal differentially, and in this regard, the sense amp circuitry 110 comprises a differential amplifier receiving the sensed signal S+ (e.g., E8) at its non-inverting input and the sensing reference S− (e.g., E9) at its inverting input. As one skilled in the art understands, the differential amplifier will subtract S− from S+ at its output, and so will cancel out any common mode voltage from both inputs. This can be useful for example when sensing ECAPs, as it may be useful to subtract the relatively large scale stimulation artifact from the measurement (as much as possible) in this instance. That being said, note that differential sensing may not completely remove the stimulation artifact, because the voltages at the sensing electrodes S+ and S− will likely not be exactly the same. For one, each will be located at slightly different distances from the stimulation and hence will be at different locations in the electric field 130. Thus, the stimulation artifact can still be sensed even when differential sensing is used. Examples of sense amp circuitry 110, and manner in which such circuitry can be used, can be found in U.S. Patent Application Publications 2019/0299006, 2020/0305744 and 2020/0305745; and PCT (Int'l) Patent Application Publication WO 2021/026151.

The digitized ESG signal from the ADC(s) 112—inclusive of any detected ECAPs and stimulation artifacts—is received at a feature extraction algorithm 140 programmed into the IPG's control circuitry 102. The feature extraction algorithm 140 analyzes the digitized sensed signals to determine one or more ECAP features, and one or more stimulation artifact features, as described for example in PCT (Int'l) Patent Application Publication WO 2020/251899. Such features may generally indicate the size and shape of the relevant signals, but may also be indicative of other factors (like ECAP conduction speed). One skilled in the art will understand that the feature extraction algorithm 140 can comprise instructions that can be stored on non-transitory machine-readable media, such as magnetic, optical, or solid-state memories within the IPG 100 (e.g., stored in association with control circuitry 102).

For example, the feature extraction algorithm 140 can determine one or more ECAP features, which may include but are not limited to:

a height of any peak (e.g., N1);

a peak-to-peak height between any two peaks (such as from N1 to P2);

a ratio of peak heights (e.g., N1/P2);

a peak width of any peak (e.g., the full-width half-maximum of N1);

an area or energy under any peak;

a total area or energy comprising the area or energy under positive peaks with the area or energy under negative peaks subtracted or added;

a length of the curve of the ECAP, or any portion thereof (e.g., the length of the curve from P1 to N2);

any time defining the duration of at least a portion of the ECAP (e.g., the time from P1 to N2);

a time delay from stimulation to issuance of the ECAP, which is indicative of the neural conduction speed of the ECAP, which can be different in different types of neural tissues;

peak frequencies when the ECAP is subject to frequency-domain analysis (e.g., Fourier analysis), and the size, area, ratio, etc. of such peak frequencies;

a conduction speed of the ECAP, which can be determined by sensing the ECAP as it moves past different sensing electrodes;

a rate of variation of any of the previous features, i.e., how such features change over time;

any mathematical combination or function of these variables;

Such ECAP features may be approximated by the feature extraction algorithm 140. For example, the area under the curve may comprise a sum of the absolute value of the sensed digital samples over a particular time interval. Similarly, curve length may comprise the sum of the absolute value of the difference of consecutive sensed digital samples over a particular time interval. Time intervals during which ECAPs are detected may be referenced to the start of simulation, or referenced from within the ECAP signal itself (e.g., referenced to peak N1 for example).

The feature extraction algorithm 140 can also determine one or more stimulation artifact features, which may be similar to the ECAP features just described, but which may also be different to account for the stimulation artifact's different shape. Determined stimulation artifact features may include but are not limited to:

a height of any peak;

a peak-to-peak height between any two peaks;

a ratio of peak heights;

an area or energy under any peak;

a total area or energy comprising the area or energy under positive peaks with the area or energy under negative peaks subtracted or added;

a length of the curve of the stimulation artifact, or any portion thereof;

any time defining the duration of at least a portion of the stimulation artifact;

measurements indicative of a timing between the stimulating waveform and the resulting stimulation artifact;

peak frequencies when the stimulation artifact is subject to frequency-domain analysis (e.g., Fourier analysis), and the size, area, ratio, etc. of such peak frequencies;

a rate of variation of any of the previous features, i.e., how such features change over time;

any mathematical combination or function of these variables.

Again, such stimulation artifact features may be approximated by the feature extraction algorithm 140, and may be determined with respect to particular time intervals, which intervals may be referenced to the start or end of simulation, or referenced from within the stimulation artifact signal itself (e.g., referenced to a particular peak). The feature extraction algorithm 140 may also determine more generic features about the sensed ESG signal, without parsing the signal into different components (e.g., the stimulation artifact, the ECAP, etc.), and then determining features of those components.

Once the feature extraction algorithm 140 determines one or more of these features, it may then be used to any useful effect in the IPG 100, and specifically may be used to adjust the stimulation that the IPG 100 provides, for example by providing new data to the stimulation circuitry 28 via bus 118. This is explained further in some of the U.S. patent documents cited above.

Sensing of stimulation artifacts to provide useful information in an IPG 100 is particularly intriguing, because such signals are generally larger and easier to sense (compared with smaller-signal neural response, such as ECAPs). In this regard, the inventors have investigated the use of sensed situation artifacts to help determine patient posture or activity (hereinafter referred to as "posture" for short). As a patient changes posture, the electrode array 17 will change in the spinal column environment. For example, the array 17, or the individual leads comprising the array, may move relative to the tissue. Such movement may bring the electrodes 16 closer to or farther away from the spinal cord, and may change the lateral positioning (e.g., the X-Y position) of electrodes relative to the spinal cord. If the electrode array 17 comprises one or more leads, posture-induced movement may also affect the position of the leads relative to each other. Furthermore, such movement may slightly change the positioning of the sensing electrodes relative to the electrodes used to provide the stimulation (e.g., if the leads bend). When one considers that the spinal column environment is comprised of different materials having different electrical characteristics (e.g., conductivities), it is perhaps not surprising that such posture-induced movement affects the stimulation artifacts that are sensed. See, e.g., PCT (Int'l) Patent Application Publication WO 2020/251899. Once patient posture is known via sensing, the stimulation provided by the IPG 100 can be adjusted appropriately to compensate for such movement, such as by adjusting its intensity, or by adjusting its lateral position within the electrodes array 17—i.e., by adjusting the electrodes used to provide the stimulation.

However, while sensing stimulation artifacts may be useful to determining patient posture (and adjusting stimulation), this doesn't inform as to which electrodes 16 in the array 17 should be used for sensing. IPG 100 is flexible, enabling any of the electrodes to be used for stimulation and any of the electrodes to be used for sensing, as described earlier. It may not be known for a given stimulation therapy (e.g., stimulation provided at certain stimulating electrodes) which electrodes would be best used as sensing electrode(s). Further, this problem may be compounded, because as noted carlier sensing may be differential, involving the selection of two electrodes S+ and S−. In short, the inventors consider it a problem to know which of the electrodes to select as the sensing electrode(s) for a given stimulation therapy.

Solutions to this problem are provided in the disclosed sensing electrode selection algorithm 150, which operates to automatically select optimal sensing electrode(s) in the electrode array for use with the patient's stimulation therapy. Algorithm 150 is shown in flow chart form in FIG. 6, and different steps in the algorithm, as well as certain alternatives, are shown in FIGS. 7A-11. Not all steps illustrated in FIG. 6 are necessary to the performance of algorithm 150, and additional steps could also be added to the algorithm 150. Further, it is not necessary that the steps be performed in the order illustrated in FIG. 6, as the order of the steps can vary.

Algorithm 150 is preferably performed during a patient fitting procedure, such as when the patient is in a clinician's office. In this regard, algorithm 150 may be implemented as part of the clinician programmer software 66 operable in a clinician programmer 50 (FIG. 4), although as described further below the algorithm 150 programs the IPG 100 and directs it to provide stimulation artifact measurements taken during the fitting procedure. Algorithm 150 may also be implemented in a patient external controller 45. The description of the algorithm 150 in FIG. 6 assumes that an external device (either the clinician programmer 50 or external controller 45) is used to start the algorithm (e.g., using its GUI 64, FIG. 4), to program the IPG during the procedure, to analyze the resulting measurements, and to ultimately program the IPG 100 with the selected sensing electrodes based on the results of the analysis. However, algorithm 150 can also operate automatically within the IPG 100 without the assistance of an external device. Algorithm 150 may comprise instructions stored in a non-transitory computer-readable media in these external devices or the IPG 100, such as by being stored in memory associated with their control circuitries.

By way of overview, and in a preferred example, the disclosed sensing electrode selection algorithm 150 preferably senses stimulation artifacts and determines one or more features of the sensed stimulation artifacts, preferably in response to a pre-determined stimulation therapy appropriate for the patient. The algorithm 150 senses the stimulation artifacts using different candidate sensing electrodes, and in this regard electrodes used to provide the stimulation therapy may be excluded. Because stimulation artifact sensing preferably occurs differentially, the different selected sensing electrodes may comprise different sensing electrode pairs, with one electrode in the pair comprising sensing electrode S+ and the other sensing reference S−. Preferably all candidate S+/S− sensing electrode pairs are used to sense stimulation artifacts during algorithm 150 in response to the stimulation therapy.

As well as sensing at different sensing electrodes/pairs, sensing of stimulation artifacts during the algorithm 150 preferably occurs with the patient placed in two or more postures. The algorithm 150 can then process the stimulation artifact features measured at the different sensing electrode pairs and at the different postures, with the goal of determining one or more sensing electrode pairs S+/S− that best distinguishes the two or more postures. As such, the algorithm 150 is able to automatically determine which electrodes in the electrode array 17 should be used for sensing given the pre-determined stimulation therapy, with the further benefit that the selected sensing electrodes are optimized to distinguish between the two or more postures.

Thereafter, the IPG 100 can be programmed with the stimulation therapy and with the determined optimal sensing electrodes to allow the stimulation artifact features to be determined during therapeutic use of the IPG 100 by the patient. During therapeutic use, the IPG 100 can determine the patient's posture using the determined stimulation artifact features, and take appropriate action such as by adjusting the therapy accordingly. If necessary, the algorithm 150 can be re-executed to adjust the selected sensing electrodes, which may be warranted for example if the stimulation therapy is later changed.

Figures 1, 2A, 2B:
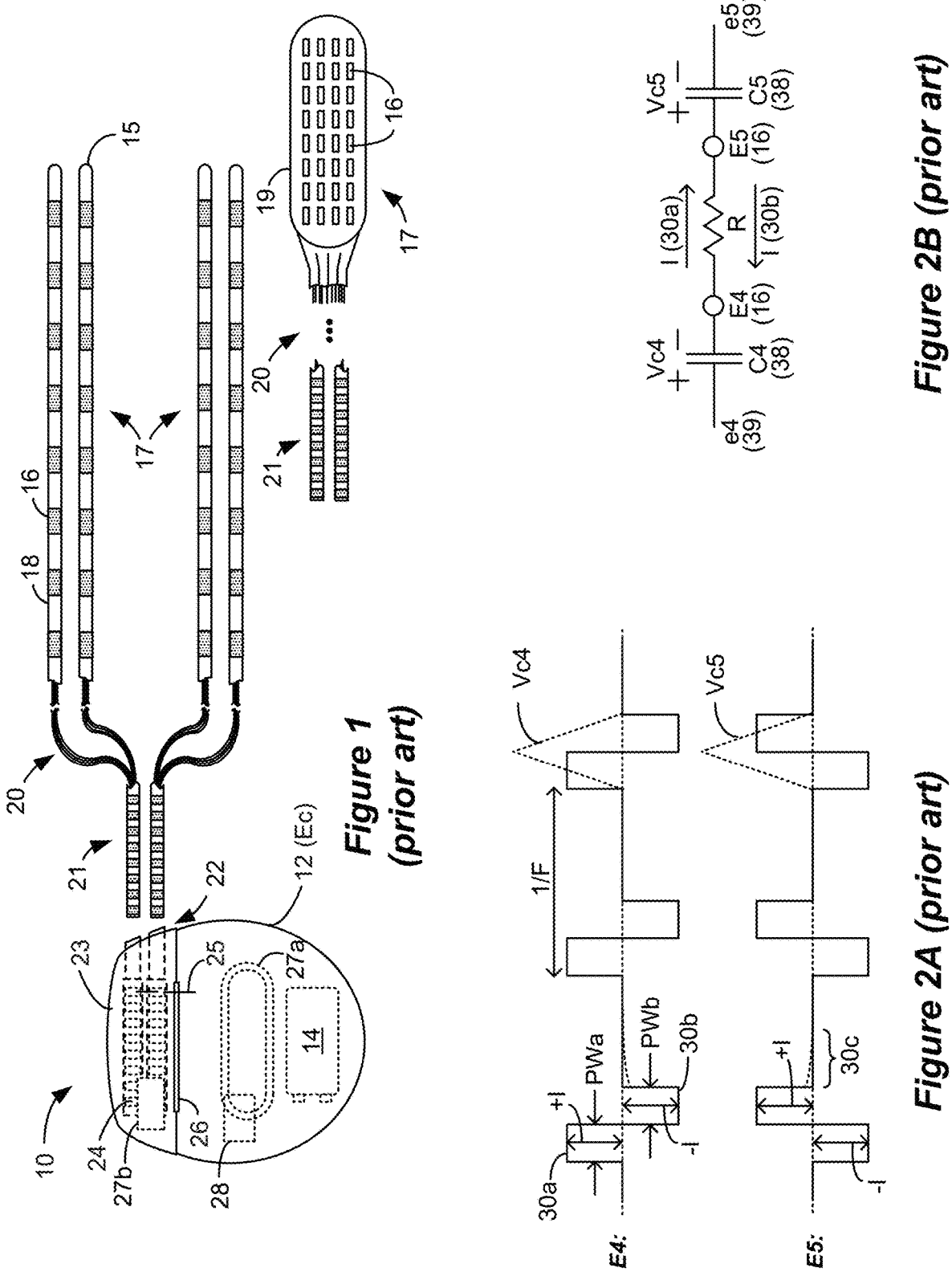
FIG. 1 shows an Implantable Pulse Generator (IPG), in accordance with the prior art.
FIGS. 2A and 2B show an example of stimulation pulses producible by the IPG, in accordance with the prior art.

In FIG. 6, it is assumed that stimulation therapy appropriate for the patient (or at least a possible candidate stimulation therapy) has been pre-determined (152), which can may have occurred using the clinician programmer's GUI 64 (FIG. 4) for example. In this example, the stimulation therapy involves providing pulses to electrodes E2 and E3 in an electrode array 17. The electrode array 17 is shown as comprising two eight-electrode leads, but this is just an example, and algorithm 150 can be used with other electrode arrays (one lead, more than two leads, paddle leads, etc.). The stimulation therapy in this example comprises a bipole, which is established using actively-driven biphasic pulses at electrodes E2 and E3, similar to what was described earlier with respect to FIG. 2A. However, the stimulation therapy can comprise any prescribed therapy, involving the selection of any number of electrodes (e.g., tripolar stimulation, monopolar stimulation), and using pulses of any particular type (actively or passive driven, etc.).

Next, the external device, such as the clinician programmer 50, receives an instruction to begin operation of the algorithm 150, which can also occur using the device's GUI 64 (FIG. 6, 154).

At this point, it may be reasonable to determine candidate sensing electrodes based on the given stimulation therapy, and the type of sensing (differential or single-ended) that will be used (FIG. 6, 156), as this will affect a feature matrix or vector that is populated by the algorithm, such as the feature matrix shown in FIG. 7A which is discussed in detail below. For example, if differential sensing is used, as FIG. 7A assumes, candidate sensing electrodes are selected in pairs S+/S−, and in this regard it may not be necessary to test all candidate S+/S− pairs. Differential sensing implies the selection of different electrodes, and therefore S+/S− combinations involving the same electrode (e.g., E1/E1) can be denoted as don't care values (x) in FIG. 7A. Further, it is logical to exclude sensing electrode pairs that would include electrodes selected to provide the stimulation therapy (e.g., E2, E3), which are also denoted as don't care values in FIG. 7A. This being said, all potential pairs could also be selected as candidate pairs without disregarding any of the pairs before the fact; any pairs providing invalid results can be ignored, as discussed further below.

Still further, given the symmetry involved in differential sensing, it may only be necessary to select sensing electrode pairs occurring on one side of the diagonal in the feature matrix of FIG. 7A. For example, when selecting electrodes E6 and E7 as a differential pair, it may not matter which of these electrodes comprises the sensing electrodes (S+) and which comprises the sensing reference (S−), because the sense amp circuitry 110 (FIG. 5) will compute the difference between the two in either instance. Ideally then, the measurements for S+/S− pairs E6/E7 and E7/E6 should have the same absolute values (e.g., 0.05V), and it may therefore not be necessary to test both of these combinations (which merely flips the inputs to the sense amp circuitry 110). Having said this, FIG. 7A and subsequent matrices show symmetrical values on both sides of matrix diagonals for completeness. If there are non-idealities that might cause the sense amp circuit 110 to measure stimulation artifacts differently for pairs Ex/Ey and Ey/Ex, it may be useful to measure them both as this may provide additional useful information for the sensing electrode selection algorithm 150 to consider.

Next, the sensing electrode selection algorithm 150 may prescribe one or more features that the IPG 100 is to sense during the algorithm (FIG. 6, 158). In the examples of FIGS. 7A-8D, it is assumed that a single feature—namely stimulation artifact maximum amplitude—will be sensed, although different features, and possibly additional features, may also be sensed during operation of the algorithm 150, as explained further below.

Next (FIG. 6, 160), the algorithm 150 can program the patient's IPG 100 with the stimulation therapy (FIG. 6, 152), the determined candidate sensing electrodes (FIG. 6, 156), and the one or more sensed features that the IPG 100 will monitor during operation of the algorithm 150 (FIG. 6, 158). This allows the IPG 100: to provide the stimulation therapy (via the PDAC/NDAC circuitry, FIG. 4); to select the determined candidate sensing electrodes or pairs (via multiplexer 108, FIG. 4); to determine the one or more features (via feature extraction algorithm 140, FIG. 4); and to transmit the measured features to the external device for analysis and for population in a feature matrix (FIG. 6, 162). Note that the IPG 100 may also simply sense the stimulation artifact and provide it as a digitized waveform to the external device. In this regard, the external device may include the feature extraction algorithm 140 instead of the IPG.

FIG. 7A shows a first example of the resulting feature matrix (Feature Matrix 1), each element of which comprises a differentially-sensed stimulation artifact maximum amplitude using the different candidate sensing electrode pairs S+/S−. Such maximum amplitudes will vary depending on many different factors as discussed earlier, and in particular will vary depending on the distance of the sensing electrode in each pair from the stimulating electrodes, and the distance of the sensing electrodes form each other. For example, the maximum differentially-sensed amplitude at pair E1/E16 is relatively large (1.39V), because E1 is close to the stimulation (e.g., E2) where the stimulation artifact would be larger, while E16 is far from the stimulation where the stimulation artifact would be smaller, which yields a large differential between the two. E10 and E11 are relatively close to the stimulation, and so the stimulation artifact at these electrodes would both be relatively large, but this would yield a small differential (0V) between the two. To generally show the magnitude of the features in FIG. 7A, higher values (≥1.0 V) are shaded in darker grey, medium values (≥0.45 V but <1.0V) are shaded in lighter grey, while smaller values (<0.45V) are unshaded. It should be noted that the stimulation artifact features shown in FIG. 7A and in subsequent figures are idealized as is useful in explaining the operation of sensing electrode selection algorithm 150. Actual values measured in a realistic example would be different. Note that each element in the feature matrix can comprise a single measured feature, or could comprise the average of a plurality of such measured features to improve measurement accuracy.

It should be noted that not all sensing electrode pairs tested may yield feature values that are valid, and if so the algorithm 150 may set such elements to don't care values in the feature matrix (although this isn't shown in FIG. 7A). The extent to which such features are valid may depend on several factors, including the specifications of the sense amp circuitry 110. For example, the sense amp circuitry 110 may only be able to handle inputs with voltages S+ and S− below a first threshold (e.g., 4V), and/or may only be able to resolve a voltage difference between these inputs (S+ minus S−) below a second threshold (e.g., 1.7V). If the sense amp circuitry 110 saturates in either of these regards—e.g., because S+ or S− is too close to the stimulating electrodes— its output would be invalid. Typically, the sense amp circuitry 110 will be able to determine when its specifications have been exceeded, and can in turn inform the algorithm 150 of such invalid feature determinations so that these elements can be discluded from the feature matrix (e.g., marked as don't care values). Note that such invalid entries are useful for the algorithm 150 to determine: the goal of the algorithm 150 is to determine one or more best sensing electrodes, and this goal is furthered by excluding sensing electrodes or pairs which yield invalid results. In short, electrodes may be excluded for which the stimulation arti- fact (or other factors) saturates the sensed signal. Note that such exclusion may be determined and occur earlier in the algorithm 150 (FIG. 6, 156).

During sensing electrode selection algorithm 150, the stimulation artifact features are determined with the patient in a particular posture, i.e., while standing (Feature Matrix 1). This is followed by taking the same measurements with the patient in one or more different postures (FIG. 6, 161). Thus, FIG. 7B shows another feature matrix populated with determined stimulation artifact features taken while the patient is sitting (Feature Matrix 2). For the reasons explained earlier, this different posture will change the environment of the electrode array 17 in the patient, result- ing in different stimulation artifact feature values. The shading used in FIGS. 7A and 7B should make these differences easier to visualize between the standing and sitting postures. Again, the values shown in FIG. 7B are idealized, and are not necessarily representative of how the measured features would be expected to change between the standing (FIG. 7A) and sitting (FIG. 7B) postures. As noted earlier, "posture" can additionally refer to activities, and so algorithm 150 can take feature measurement with the patient involved in different activities as well (e.g., walking).

FIG. 7C assumes an implementation of sensing electrode selection algorithm 150 in which sensing electrodes will be selected based on the assessment of only two postures (standing v. sitting); later figures will illustrate a more complicated example in which three or more postures are assessed. In FIG. 7C, the algorithm 150 continues by taking the feature matrices for the two tested postures (standing, FIG. 7A; and sitting, FIG. 7B) and subtracting them on an element-by-element basis to compute a difference matrix between these two postures (Difference Matrix 1) (FIG. 6, 164). The difference matrix may comprise an absolute value of these differences, because only the amount of the difference may matter. Next, the algorithm 150 assesses the elements in the difference matrix to determine the sensing electrode pair that yields the largest difference in the stimu- lation artifact feature between the two postures, with this pair being optimal to use for sensing given the stimulation therapy (FIG. 6, 166). In the example of FIG. 7C, this largest difference (0.25 V) occurs for sensing electrode pair E7/E10 (or E10/E7 as these are assumed symmetrical for the reasons stated earlier).

Although FIG. 7C does not reflect this, note that it is possible that the difference matrix could reflect other sensing electrode pairs having the same maximum difference (0.25V), and therefore the algorithm 150 may determine more than one sensing electrode pair to be optimal. Although not shown, the algorithm 150 could include additional steps to determine which one of multiple optimal sensing elec- trode pairs to use based on different factors. For example, the algorithm 150 may prefer to use a sensing electrode pair having the largest values for the features (in FIGS. 7A and 7B) because these might be most reliably sensed.

Looking back at the individual feature matrices (FIGS. 7A and 7B), notice that the stimulation artifact feature measured using this optimal sensing electrode pair E7/E10 is not necessarily the strongest signal at any given posture. For example, in FIG. 7A (standing) the feature is only 0.25V, and in FIG. 7B (sitting) the feature is only 0.5V, which values are significantly lower than those measured at other sensing electrodes pairs. Still, the difference (FIG. 7C) in this feature is largest when this sensing electrode pair E7/E10 is used, suggesting that this sensing electrode pair should be selected for sensing given the patient's stimulation therapy. This sensing electrode pair provides valid data, and more importantly is most sensitive to changes between the two postures, and thus best able to determine which posture the patient is in (standing or sitting). As taught in the art, once the patient's posture is known, the patient's stimulation therapy can be adjusted to compensate for posture-induced movement of the electrodes array 17 in the spinal environ- ment, as explained further below.

As noted earlier, FIGS. 7A-7C disclose an example in which the sensing electrode selection algorithm 150 selects sensing electrodes based on the assessment of only two postures. However, more than two postures can also be considered, as shown in FIGS. 8A-8D. In this more-com- plicated example, three postures—standing, sitting, and supine (lying on one's back)—are considered, and the sensing electrode selection algorithm 150 populates feature matrices with the patient in each of these postures (FIGS. 6, 161 and 162). The feature matrices for standing (Feature Matrix 1) and sitting (Feature Matrix 2) were already shown in FIGS. 7A and 7B. An additional feature matrix populated with stimulation artifact feature measurements taken with the patient while supine is shown in FIG. 8A (Feature Matrix 3). Again, the measured features populated in the supine feature matrix of FIG. 8A are idealized, but are slightly different from the values populated in the standing and sitting matrices.

Next, and as shown in FIG. 8B, a number of difference matrices are populated, with each reflecting difference in the measured feature between two of the postures (FIG. 6, 164). Because there are three different postures tested in this example, there are three possible difference matrices: Dif- ference Matrix 1, reflecting the absolute value of the differ- ence of the features in the standing (FIG. 7A) and sitting (FIG. 7B) feature matrices (shown earlier in FIG. 7C, but reproduced for convenience in FIG. 8B); Difference Matrix 2, reflecting the absolute value of the difference between the standing (FIG. 7A) and supine (FIG. 8A) feature matrices; and Difference Matrix 3, reflecting the absolute value of the difference between the sitting (FIG. 7B) and supine (FIG. 8A) feature matrices. More than three postures could be used and tested as well during algorithm 150, which would result in a growing number of difference matrices. For example, if four postures are tested, six difference matrices can be determined between any two postures; if five postures are tested, ten difference matrices can be determined, as one skilled in the art will appreciate.

Next steps in the sensing electrode selection algorithm 150 are designed to determine which sensing electrode pairs have the most significant variation between the postures, which involves an assessment of which elements in difference matrices have the largest variation (FIG. 6, 168). This determination can be accomplished in different ways, with FIGS. 8C and 8D showing a particular example. In FIG. 8C, the values in each of the difference matrices are added on an element-by-element basis, yielding a Summed Difference Matrix (FIG. 6, 170). For example, and using the element corresponding to sensing electrode pair E7/E16, the sum is 0.32, because the values of this element in Difference Matrices 1, 2, and 3 (FIG. 8B) are 0.16, 0.06, and 0.1 respectively.

Next, in FIG. 8D, these summed values are multiplied by the minimum difference values for each element (i.e., a minimum of the addends), yielding a Weighted Difference Matrix (FIG. 6, 172). Again using the element corresponding to sensing electrode pair E7/E16 as an example, the minimum difference value from the difference matrices (0.16, 0.06, and 0.1) is 0.06, which is multiplied by the sum of 0.32, yielding 0.019 as shown.

The algorithm 150 can then determine a largest of these weighted difference values, and determine the sensing electrode pair corresponding to this largest value to be optimal (FIG. 6, 174). In FIG. 8D, the largest weighted difference value is 0.09, which corresponds to sensing electrode pair E1/E7. As a result, algorithm 150 would in this example select these sensing electrodes for use with the stimulation therapy, as this electrode pair is best able to distinguish the three postures from another. If there is more than one element in the Weighted Difference Matrix with a highest value, the algorithm 150 may determine more than one sensing electrode pair to be optimal, and could take further steps to select a best of those optimal pairs.

Multiplying the sums by the minimum difference (FIG. 6, 172) tends to give emphasis to difference values that are most significant between the different postures. For example, the difference matrices (FIG. 8B) might for a given element (a given sensing electrode pair) reflect a difference of 0.15 in the measured feature between standing and sitting; a difference of 0.15 between standing and supine; and a difference of 0 between sitting and supine. These differences are significant to distinguish sitting and supine from standing (0.15), but do not well distinguish between all possible postures, such as sitting and supine (0). As a result, this sensing electrode pair would be deemphasized (by multiplying the sum by the minimum difference value of 0) because it does not reliably distinguish between all possible postures tested.

It is interesting to note that the optimal sensing electrodes that the algorithm 150 selects—E1/E7 in this example—are not necessarily the best to distinguish between any two of the postures. Referring again to FIG. 8B, note that the largest feature difference in Difference Matrix 1 (0.25) corresponds to sensing electrode pair E7/E10, suggesting that this pair would best distinguish between standing and sitting. The largest feature difference in Difference Matrix 2 (0.3) corresponds to sensing electrode pair E4/E13, suggesting that this pair would best distinguish between standing and supine. The largest feature difference in Difference Matrix 3 (0.3) corresponds to a number of different electrode pairs E1/E7, E4/E13, and E5/E13, suggesting that any one of these pairs would best distinguish between sitting and supine. Nonetheless, E1/E7 best distinguishes between each of the combinations of postures, and therefore is the optimal choice for sensing, even though this sensing electrode pair is not necessarily optimal to distinguish between any two given postures.

The sensing electrode selection algorithm 150 preferably determines which sensing electrode pairs have the most significant variation between the postures (FIG. 6, 168), with FIGS. 8C and 8D illustrating one manner in which this determination can be made. However, different mathematics or statistics could be applied to the individual feature matrices, and/or the difference matrices, to assist in making this determination. In this regard, the Weighted Difference Matrix may be understood as an example of a cost function representative of the ability of a sensing electrode pair to differentiate between postures while mitigating extraneous values. The cost function could be formulated differently and could potentially be non-linear. For example, the cost function (i.e., the values in the Weighted Difference Matrix) could be computed as a ratio in which a minimum difference between the postures is provided in the numerator, and the product of all differences between the various postures is provided in denominator. In this example, the optimal sensing pair(s) would comprise that corresponding to a lowest value(s) in the Weighted Difference Matrix. In another example, the Weighted Difference Matrix could involve calculation of a sum of differences between the various postures, with this sum being raised to an exponent equal to a minimum difference between the postures. Again, in this example, the optimal sensing pair(s) would comprise that corresponding to the lowest value(s). The cost function could also involve computations made from matrices involving one or more different determined features, as discussed further below with respect to FIGS. 9A-9C. Selection of the optimal sensing electrode pair(s) could also involve more-sophisticated machine-learning algorithms (gradient descent, particle swarm, simulated annealing) that use a differently formulated and potentially non-linear cost function. The reader should thus appreciate that FIGS. 8C and 8D only provide a simple example of a manner in which one or more optimal sensing electrodes pairs can be selected by comparing difference between the postures; other methods are possible.

Sensing electrode selection algorithm 150 may also consider more than one feature of the stimulation artifacts that are sensed (FIG. 6, 158). To this point, it has been assumed that the algorithm 150 determines and considers a particular feature of the sensed stimulation artifacts, such as maximum stimulation artifact amplitude. But the feature extraction algorithm 140 in the IPG 100 (FIG. 5) can determine more than one feature of sensed stimulation artifacts, such as the area under the stimulation artifact curve, the length of the stimulation artifact curve, and other features mentioned previously. Detection of more than one feature can allow the sensing electrode selection algorithm 150 to determine not just the electrodes to use for sensing, but the feature that should be sensed by the feature extraction algorithm 140 going forward (FIG. 6, 175). An example involving sensing more than one feature is shown in FIGS. 9A-9C. FIG. 9A shows detection of maximum stimulation artifact amplitude (Feature A), and largely summarize steps described previously: different feature matrices are populated (1A-3A) with the differentially-sensed maximum stimulation artifact amplitude, and with the patient in different postures; difference matrices are determined (1A-3A) subtracting the values for two of the postures, and ultimately a Weighted Difference Matrix A is determined. In this example, it is assumed as before that the weighted difference matrix has a maximum value corresponding to sensing electrode pair E1/E7, which would comprise the optimal sensing electrode pair when sensing maximum stimulation artifact amplitude (Feature A).

FIG. 9B is similar to FIG. 9A, but involves the sensing of an additional stimulation artifact feature, namely the area under the stimulation artifact curve (Feature B). Feature matrices are populated (1B-3B) with the differentially-sensed values for this feature with the patient in different postures. Note that Features A and B can be determined at the same time by feature extraction algorithm 140 (FIG. 5) in the IPG 100, and so Feature matrices 1A and 1B, 2A and 2B, and 3A and 3B, can each be populated at the same time during patient testing. Difference matrices are determined for Feature B (1B-3B) as before and a weighted difference matrix for Feature B is determined (Weighted Difference Matrix B). In this example, it is assumed that the weighted difference matrix has a maximum value corresponding to sensing electrode pair E5/E13, which would comprise the optimal sensing electrode pair when sensing stimulation artifact area (Feature B). Thus, the algorithm 150 arrives at two potentially useable and optimal sensing electrode pairs: E1/E7, arrived at when detecting Feature A, and E5/E13, arrived at when detecting Feature B. The algorithm 150 may in one example use both of these results, and going forward sense both of these features at the electrode pairs suggested—i.e., to determine patient posture and adjust the stimulation therapy. That is, both pairs of sensing electrodes may be saved, because different features may be effective depending on various circumstances (e.g., electrical noise, patient posture, stimulation waveform).

The algorithm 150 may alternatively employ an analysis step 180 to pick a feature for sensing (FIG. 6, 175). Analysis step 180 is shown in one example in FIG. 9C, and can be implemented in several different ways. For example, the analysis step 180 may consider which of the features is most easy to sense (e.g., maximum stimulation amplitude may be easier for the feature extraction algorithm 140 to determine compared to stimulation artifact area). Alternatively, the analysis step 180 may assess which of the sensing electrodes and features appear to be most significant. For example, assume that the maximum value in Weighted Difference Matrix A (that corresponding to E1/E7) is significantly higher than other entries, whereas the maximum value in Weighted Difference Matrix B (that corresponding to E5/E13) is close to other high-value entries. This might suggest that analysis step 180 will pick Feature A—and its associated electrode E1/E7—for sensing, because the Weighted Difference Matrix A shows E1/E7 to be more significant than E5/E13 in Weighted Difference Matrix B. In short, in analysis step 180, the algorithm 150 can select not only the sensing electrodes, but the feature that will detected at those sensing electrodes going forward—i.e., to determine patient posture and adjust the stimulation therapy.

Note that feature determination at step 175 could be independent of, or precede, sensing electrode pair determinations, and hence could occur earlier in the algorithm 150. This alternative is sensible, because sensing electrode pair selection could depend on the feature(s) being assessed.

Returning to FIG. 6, once the optimal sensing electrodes/pairs have been determined (166, 168), and optionally if the feature to be sensed is also determined (175), the sensing electrodes selection algorithm 150 can thereafter program the IPG 100 with these determinations (176) so that the IPG 100 sense appropriately during therapeutic use of stimulation therapy for the patient. For example, and referring to FIG. 13, the determined sensing electrodes/pairs can be stored in memory 190 associated with the IPG's control circuitry 102, and used to select the appropriate sensing electrodes S+ and S− via bus 114. Similarly, the determined feature can be stored in memory 192, which can inform the feature extraction algorithm 140 as to features in the ESG signal (maximum stimulation artifact amplitude, etc.) it should determine when sensing.

As noted earlier, the use of differential sensing is preferred during use of sensing electrode selection algorithm 150 and going forward to determine patient posture. However, this is not strictly necessary, and FIG. 10 shows an example in which single-ended sensing of features is used. As noted earlier, single-ended sensing senses a signal at a given electrode S+, while sensing reference S− comprises a fixed reference voltage, such as Vamp. Sensing electrode algorithm 150 thus in this example seeks to determine not a differential pair of sensing electrodes S+/S−, but a single sensing electrode S+ for use. This changes the data structures discussed earlier from matrices to vectors. Thus, and as shown in FIG. 10, feature vectors are populated (FIG. 6, 162), comprising the non-differential measurements of a given stimulation artifact feature, assumed in this example to be maximum stimulation artifact amplitude. As before, this feature is sensed with the patient in different postures (FIG. 6, 161), with Feature Vector 1 populating feature measurements made while standing, Feature Vector 2 populating feature measurements made while sitting, and Feature Vector 3 populating feature measurements made while supine. (Again, other stimulation artifact features like stimulation artifact area could be used, and could be used in addition to other sensed features as discussed with reference to FIGS. 9A-9C).

Difference vectors are then determined comparing two of the postures (FIG. 6, 164), similar to what occurred for the matrices discussed earlier. Thus, Difference Vector 1 comprises the absolute value of the difference between the standing and sitting features; Difference Vector 2 comprises the absolute value of the difference between the standing and supine features; and Difference Vector 3 comprises the absolute value of the difference between the sitting and supine features. A Summed Difference Vector is then determined by summing the difference vectors on an element-by-element basis (FIG. 6, 170), and a Weighted Difference Vector is then determined by multiplying that sum by the minimum value of the elements comprising each sum (FIG. 6, 172). The largest value in the Weighted Difference Vector is determined, and the electrode associated with that largest value is determined by the algorithm 150 as the optimal sensing electrode (FIG. 6, 174), because this electrode best differentiates between each of the possible combinations of postures. In the example of FIG. 10, the electrode corresponding to this largest weighted difference (0.015) is E5.

To this point, it has been assumed that the sensing electrode selection algorithm 150 senses stimulation artifacts and determines stimulation artifact features when determining one or more optimal sensing electrodes to be used given a particular stimulation therapy for a patient. As noted earlier, sensing of stimulation artifacts is preferred, because such artifacts are relatively large and easier to sense.

However, the algorithm 150 is not so limited and could use features determined from other sensed signal as well, including ECAPs which also can comprise part of the sensed ESG signal as explained earlier. This example is shown in FIG. 11, and is similar to other examples in which feature matrices are populated with the patient in different postures. However, in this example, the sensed feature comprises an ECAP feature, such as ECAP peak-to-peak amplitude. As noted earlier, the feature extraction algorithm 140 (FIG. 5) in the IPG 140 can determine this and other ECAP features. As before, feature matrices, difference matrices, a summed difference matrix, and a weighted difference matrix are determined, with the largest value(s) in this last matrix used to determine sensing electrode(s) that are optimal for the given stimulation therapy. Going forward during therapeutic use, the IPG can continue to sense this ECAP feature at the determined optimal sensing electrodes to determine patient posture and adjust the stimulation therapy as necessary.

As noted above, a purpose of sensing electrode selection algorithm 150 is to automatically determine optimal sensing electrodes/pairs for use with a given stimulation therapy, and preferably optimal sensing electrodes/pairs that can distinguish between different patient postures. Data taken during execution of algorithm 150 can also be used to assist the IPG 100 in determining the different postures once the sensing electrodes/pairs have been determined. In particular, such data can be used to set thresholds for the sensed features. In this regard, FIG. 12 shows a posture threshold algorithm 200, which is used to determine one or more threshold ranges for sensed features, and to program the IPG 100 with those threshold ranges to allow the IPG to determine posture using the optimal sensing electrodes/pairs. Posture threshold algorithm 200 is shown separately from the sensing electrode selection algorithm 150 for simplicity, although the two can be used together in a single algorithm in other implementations. It is again assumed that the posture threshold algorithm 200 is stored in and executed by an external device (e.g., clinician programmer 50) during a fitting procedure, but the posture threshold algorithm 200 may also be stored in and executed by the IPG 100 itself.

As a first step (202), the posture threshold algorithm 200 determines values from the feature matrices for the optimal sensing electrodes or pairs determined during use of the sensing electrode determination algorithm 150. FIG. 12 shows these values for various of the examples shown in earlier figures. For example, the left example considers FIG. 7C where optimal sensing electrodes were selected (E7/E10) using differential sensing, and based on fitting with the patient in two different postures (standing and sitting). At this sensing electrode pair, the features from the feature matrices are 0.25 (FIG. 7A, standing) and 0.5 (FIG. 7B, sitting). The middle example considers FIG. 8D where optimal sensing electrodes were selected (E1/E7) using differential sensing, and based on three different postures (standing, sitting, and supine). At this sensing electrode pair, the features from the feature matrices are 1.35 (FIG. 7A, standing), 1.25 (FIG. 7B, sitting), and 1.5 (FIG. 8A, supine). The right example considers FIG. 10 where an optimal sensing electrode is selected (E5) using single-ended sensing, and based on three different postures (standing, sitting, and supine). At this sensing electrode, the features from the relevant vectors (FIG. 10) are 3.2 (standing), 3.1 (sitting), and 3.05 (supine).

The posture threshold algorithm 200 can then determine threshold(s) and associated ranges for each posture (204), and program the IPG 100 with these threshold ranges (206). In all cases, it is assumed that suitable thresholds would be the midpoints of the values pulled from the feature matrices (202), but this is only for simplicity to illustrate the technique, and the thresholds could be set differently. More broadly, step 204 could involve any clustering, machine learning, or general classification method capable of discerning and prescribing ranges for the "state" of the sensing electrodes from the sensed features.

For example, the values in the left example comprises 0.25 for standing, and 0.5 for sitting. Therefore, a midpoint threshold, T1=0.375, can be determined to allow the IPG to differentiate standing from sitting. In this example, if the sensed feature falls within a range T>T1, the IPG 100 can conclude that the patient is sitting, and if T≤T1, the IPG can conclude that the patient is standing. In the middle example, where the values were 1.35 (standing), 1.25 (sitting), and 1.5 (supine), midpoint thresholds of T1=1.30 (between 1.25 and 1.35) and T2=1.425 (between 1.35 and 1.5) are determined. If the sensed feature T>T2, the IPG 100 can conclude that the patient is supine; if T<T1, the IPG can conclude that the patient is sitting; and otherwise, if T1<T<T2, the IPG can conclude that the patient is standing. In the right example, where the values were 3.2 (standing), 3.1 (sitting), and 3.05 (supine), midpoint thresholds of T1=3.15 (between 3.1 and 3.2) and T2=3.075 (between 3.05 and 3.1) are determined. If the sensed feature T>T2, the IPG 100 can conclude that the patient is standing; if T<T1, the IPG can conclude that the patient is supine; and otherwise, if T1<T<T2, the IPG can conclude that the patient is sitting. Once these thresholds ranges are determined for each posture, they can be programmed into the IPG 100 (206).

Such programming of the IPG 100's circuitry is shown in FIG. 13 using the middle example of FIG. 12. The determined threshold ranges and associated postures are stored in a threshold analysis module 210, which can comprise instructions programmed into the IPG 100's control circuitry 102. During therapeutic use of the IPG to provide the stimulation therapy, the ESG signal is periodically sensed at the optimal sensing electrodes (190) for that therapy, and the feature extraction algorithm 140 determines a relevant sensed feature T in accordance with the programmed feature (192). The sensed feature T is provided to the threshold analysis module 210 where it is compared against the determined thresholds T1 and T2 to see which threshold range it falls in, which then informs as to the patient's current posture.

Once posture has been determined, the IPG 100 can take any desired action, including adjusting the therapy as appropriate for the posture. In the example shown, it is assumed that each posture (sitting, supine, standing) is associated with a stimulation program SP (A, B, C) in the threshold analysis module 210. The stimulation program associated with the determined posture can then be automatically executed by the IPG 100's stimulation circuitry 28 via bus 118. Stimulation programs may comprise adjustments to the prescribed stimulation therapy. For example, each stimulation program may specify a different stimulation amplitude, pulse width, or frequency, or may involve the selection of new stimulating electrodes. Note that the stimulation programs in threshold analysis module 210 may be determined by experimentation during the fitting procedure: that is, best stimulation programs or adjustments for each posture may be determined for the patient when placed in the different postures, and then stored in the module 210. (This detail was omitted from the illustration of sensing electrode selection algorithm 150 in FIG. 6).

It would be expected that stimulation programs or adjustments specified in threshold analysis module 210 would normally comprise relatively minor changes to the predetermined stimulation therapy, such that the sensing electrodes/pairs determined earlier (via algorithm 150) can be used with each program. However, this is not strictly necessary. Instead, although not illustrated, sensing electrodes/pairs and features can also be determined for each of the postures and associated stimulation programs, which would allow sensing to be adjusted by the threshold analysis module 210 as the stimulation programs are adjusted.

Although particular embodiments of the present invention have been shown and described, the above discussion is not intended to limit the present invention to these embodiments. It will be obvious to those skilled in the art that various changes and modifications may be made without departing from the spirit and scope of the present invention. Thus, the present invention is intended to cover alternatives, modifications, and equivalents that may fall within the spirit and scope of the present invention as defined by the claims.

What is claimed is:

1. A method for programming a stimulator device, the stimulator device comprising a plurality of electrodes configured to contact a patient's tissue, the method comprising:
   (a) determining stimulation to be applied at at least two of the electrodes;
   (b) sensing a response to the stimulation at a plurality of combinations of the electrodes with the patient in different postures;
   (c) for each of the plurality of combinations, determining at least one difference in the sensed response between two of the postures, and using the at least one difference at each of the plurality of combinations to determine one or more optimal of the combinations; and
   (d) programming the stimulator device with the one or more optimal combinations to be used for sensing with the stimulation.

2. The method of claim 1, wherein the sensed response comprises a stimulation artifact, wherein the stimulation artifact comprises a signal formed by an electric field induced in the tissue by the stimulation.

3. The method of claim 1, wherein the sensed response comprises a neural response formed by recruitment of neural fibers in the tissue in response to the stimulation.

4. The method of claim 1, wherein the plurality of combinations exclude the at least two electrodes to which the stimulation is to be applied.

5. The method of claim 1, wherein steps (a), (c), and (d) are performed using an external device in communication with the stimulator device.

6. The method of claim 1, wherein the method is performed within the stimulator device.

7. The method of claim 1, wherein the sensed response is sensed differentially using both of the electrodes in each of the combinations.

8. The method of claim 1, wherein there are two postures, and wherein for each of the plurality of combinations, a single difference in the sensed response is determined between the two postures, wherein the single difference at each of the plurality of combinations is used to determine the one or more optimal combinations.

9. The method of claim 8, wherein the one or more optimal combinations are determined as one or more combinations having a largest of the single difference.

10. The method of claim 1, wherein there are three or more postures.

11. The method of claim 10, wherein for each of the combinations, a plurality of differences in the sensed response is determined between two of the three or more postures, wherein the plurality of differences at each of the plurality of combinations is used to determine the one or more optimal combinations.

12. The method of claim 11, further comprising summing the plurality of differences for each of the plurality of combinations.

13. The method of claim 12, further comprising multiplying the summed difference by a minimum of the addends to form a weighted value for each of the plurality of combinations, wherein the one or more optimal combinations are determined as the one or more combinations having the largest weighted value.

14. The method of claim 1, wherein the stimulator device comprises a Spinal Cord Stimulator device.

15. The method of claim 1, further comprising after step (d):
   (e) sensing a response to the stimulation at the determined one or more optimal combinations; and
   (f) determining a posture of the patient using the sensed response at step (e).

16. The method of claim 15, further comprising:
   (g) adjusting the stimulation in accordance with the determined posture.

17. An external device for programming a stimulator device, the stimulator device comprising a plurality of electrodes configured to contact a patient's tissue, the external device comprising:
   control circuitry configured to:
   (a) determine stimulation to be applied at at least two of the electrodes;
   (b) receive a response to the stimulation at a plurality of combinations of the electrodes with the patient in different postures;
   (c) for each of the plurality of combinations, determine at least one difference in the sensed response between two of the postures, and use the at least one difference at each of the plurality of combinations to determine one or more optimal of the combinations; and
   (d) program the stimulator device with the one or more optimal combinations to be used for sensing with the stimulation.

18. A non-transitory computer readable media including instructions executable on an external device for programming a stimulator device, the stimulator device comprising a plurality of electrodes configured to contact a patient's tissue, wherein the instructions when executed are configured to:
   (a) determine stimulation to be applied at at least two of the electrodes;
   (b) receive a response to the stimulation at a plurality of combinations of the electrodes with the patient in different postures;
   (c) for each of the plurality of combinations, determine at least one difference in the sensed response between two of the postures, and use the at least one difference at each of the plurality of combinations to determine one or more optimal of the combinations; and
   (d) program the stimulator device with the one or more optimal combinations to be used for sensing with the stimulation.

* * * * *